(12) United States Patent  
Raksi

(10) Patent No.: US 10,105,260 B2  
(45) Date of Patent: Oct. 23, 2018

(54) INTEGRATED OPHTHALMIC SURGICAL SYSTEM

(71) Applicant: Novartis AG, Basel (CH)

(72) Inventor: Ferenc Raksi, Mission Viejo, CA (US)

(73) Assignee: Novartis AG (CH)

( * ) Notice: Subject to any disclaimer, the term of this patent is extended or adjusted under 35 U.S.C. 154(b) by 0 days.

(21) Appl. No.: 15/664,680

(22) Filed: Jul. 31, 2017

(65) Prior Publication Data

US 2018/0028355 A1 Feb. 1, 2018

Related U.S. Application Data

(60) Provisional application No. 62/369,631, filed on Aug. 1, 2016.

(51) Int. Cl.

| | |
|---|---|
| *A61F 9/008* | (2006.01) |
| *A61B 3/10* | (2006.01) |
| *A61B 3/13* | (2006.01) |
| *A61B 3/18* | (2006.01) |
| *A61F 9/009* | (2006.01) |
| *A61B 50/13* | (2016.01) |

(Continued)

(52) U.S. Cl.  
CPC ............ *A61F 9/008* (2013.01); *A61B 3/0075* (2013.01); *A61B 3/102* (2013.01); *A61B 3/13* (2013.01); *A61B 3/185* (2013.01); *A61F 9/009* (2013.01); *A61B 3/0025* (2013.01); *A61B 18/22* (2013.01); *A61B 50/13* (2016.02); *A61B 2017/00199* (2013.01); *A61B 2018/2277* (2013.01); *A61F 9/00836* (2013.01); *A61F 2009/00846* (2013.01); *A61F 2009/00857* (2013.01); *A61F 2009/00882* (2013.01); *A61F 2009/00887* (2013.01); *A61F 2009/00889* (2013.01); *A61F 2009/00897* (2013.01)

(58) Field of Classification Search  
CPC ........... A61B 3/14; A61B 3/0025; A61B 3/12; A61B 3/102; A61B 3/0058  
USPC ........................................................ 351/206  
See application file for complete search history.

(56) References Cited

U.S. PATENT DOCUMENTS

| | | | |
|---|---|---|---|
| 8,414,564 B2 | 4/2013 | Goldshleger et al. | |
| 8,419,721 B2 | 4/2013 | Raksi et al. | |

(Continued)

FOREIGN PATENT DOCUMENTS

| | | |
|---|---|---|
| WO | 2008/098388 A1 | 8/2008 |
| WO | 2013/000487 A1 | 1/2013 |

*Primary Examiner* — Mohammed Hasan  
(74) *Attorney, Agent, or Firm* — Keiko Ichiye, Esq.

(57) ABSTRACT

An ophthalmic surgical system includes a chassis comprising a laser source. The system includes a gantry coupled to the chassis. The position of the gantry is adjustable. The system includes a reference interface coupled to the gantry. The reference interface comprises an attachment interface at a distal portion of the reference interface, configured to couple to a patient interface for docking with an eye. The reference interface is configured to move to a first plate position proximal to the chassis and a second plate position distal from the chassis. The system further includes an optical head unit coupled to the reference interface. The optical head unit comprises a laser scanner and a beam splitter. The optical head unit is configured to move to a first head unit position near a proximal end of the reference interface and a second head unit position which is a lockable surgical position near a distal end of the reference interface.

20 Claims, 13 Drawing Sheets

(51) Int. Cl.
  *A61B 3/00* (2006.01)
  *A61B 18/22* (2006.01)
  *A61B 17/00* (2006.01)

(56) References Cited

U.S. PATENT DOCUMENTS

| | | |
|---|---|---|
| 8,500,725 B2 | 8/2013 | Raksi |
| 8,506,559 B2 | 8/2013 | Raksi |
| 8,764,737 B2 | 7/2014 | Kurtz et al. |
| 8,771,262 B2 | 7/2014 | Rathjen |
| 8,920,407 B2 | 12/2014 | Raksi et al. |
| 9,044,303 B2 | 6/2015 | Kurtz et al. |
| 2008/0234666 A1* | 9/2008 | Yadlowsky ............ A61F 9/008 606/4 |
| 2012/0089134 A1 | 4/2012 | Horvath et al. |
| 2012/0316544 A1 | 12/2012 | Horvath et al. |
| 2014/0216468 A1 | 8/2014 | Goldshleger et al. |
| 2014/0350533 A1 | 11/2014 | Horvath et al. |

\* cited by examiner

INTEGRATED OPHTHALMIC SURGICAL SYSTEM

FIELD

The present disclosure relates generally to laser-assisted ophthalmic surgical systems.

BACKGROUND

The anterior segment of the eye includes structures in front of the vitreous humor, including the cornea, iris, ciliary body, and crystalline lens. Common anterior segment disorders include cataracts and refractive errors in the cornea.

Ophthalmic surgeons may use photodisruptive laser technology in cataract and corneal procedures to improve accuracy, safety, and patient outcomes. For example, femtosecond laser systems may be used in cataract surgery for capsulorhexis and lens fragmentation via laser-induced photodisruption. Femtosecond lasers may also be used in corneal applications, such as corneal flap creation for LASIK. The LenSx® Laser System available from Alcon is an example of a femtosecond laser system that may be employed in both cataract and corneal surgical procedures. Laser systems used in a cataract procedure typically include a laser engine, an optical head unit, a dedicated OCT system and imaging device for targeting tissue and cut patterns, a monitor, and various user input mechanisms.

After a laser portion of a cataract procedure is complete, the surgeon may perform a manual procedure to remove the fragmented lens and insert an intraocular lens (IOL). In general, surgical laser systems are stand-alone systems that are functionally and structurally separate from equipment used by a surgeon during manual surgical procedures, which often includes non-sterile and sterile preparation areas, a high-resolution stereo surgical microscope, an OCT system, imaging devices, display monitors, and instrumentation for anesthesiology Due to their substantial size, it is difficult to arrange both laser and manual surgical equipment around a patient in a single operating room. An operating room for laser-assisted cataract surgery typically needs to accommodate at least five individuals: a patient, the operating surgeon, two assistants, and anesthesiologist. Moreover, the operating room must accommodate the above-referenced instruments, as well as surgical scalpels, tweezers and scissors, a manually held phacoemulsification hand-piece piece with tubing connected to a console, and an intra-ocular lens (IOL) injection device. Thus, ophthalmic surgeons often require two rooms or dedicated spaces to perform a cataract procedure—one for the laser system and procedure, and another for the manual procedure and associated instruments. Patients may be initially situated in one area beneath a laser surgical system for the laser portion of a procedure, then moved to another area beneath a surgical microscope for the manual part of the procedure. This increases the time and cost of the surgery.

Accordingly, there is a need to integrate the equipment used in a laser and manual ophthalmic surgical procedures to streamline surgeries, reduce the amount of floor space required, and eliminate costly duplicative equipment, such as OCT systems. However, properly integrating such equipment presents many challenges.

For example, the surgeon's tools require not only sufficient floor space around a patient, but a working distance under the surgical microscope and any attached imaging device. The working distance must be sufficient to permit the surgeon to perform a manual cataract procedure, but must abide the capabilities of the microscope and accommodate a comfortable posture for the surgeon. A surgeon's typical working distance (e.g., 150-300 mm) may be comparable to or smaller than the depth of a surgical laser optical head. Thus, even temporarily positioning a surgical laser optical head between a microscope and the patient's head is problematic because, in addition to the space needed for the optical head itself, additional room is needed to safely dock and maneuver the laser surgical unit very close to the patient's face and eye. But, simply increasing the working distance of a surgical microscope to accommodate a laser optical head may necessitate higher aperture optics, increased complexity, and additional costs, and may make it more difficult for a surgeon to comfortably position himself or herself during a procedure.

Integrating OCT systems used in the laser and manual portions of a procedure presents additional challenges. For instance, typically each OCT system will optimally operate at the near-infrared optical wavelength region to avoid the light being visible to the patient and the tissue being transparent. When OCT is used for pre- and post-operative diagnosis of the refractive properties of the eye, a broad bandwidth OCT light source is necessary to achieve several microns spatial resolution. The bandwidth necessary to achieve this resolution is around 100 nm or more. Most femtosecond lasers appropriate for ophthalmic surgery employs Ytterbium gain material because of their superior properties and advanced technology and operative in the wavelength band of 1025 to 1055 nm. When the two wavelength bands overlap and the light traverses parts of the same optical components, it may be problematic to separate the light beams of the two subsystems and avoid interference.

Another difficulty in integrating subsystems lies in the increased mass of the components of the integrated system, which connect to the eye of the patient. As the integrated components become heavier and bulkier, it is more difficult to safely attach them to the patient's eye and avoid mechanical injury. Systems which attempt to avoid this issue by operating in an undocked state (i.e., not attached to the eye) typically require an active eye tracking device, which increase complexity and cost and, due to involuntary eye movements, may limit the time of laser treatment to a fraction of a second. When the laser treatment time is limited, available treatment options are also limited to a subset of treatments otherwise available with a femtosecond laser. Indeed, laser treatment for cataract surgery may require incisions inside the lens and laser fragmentation of cataractous lens tissue, which may require treatment times well beyond the ability for a patient to voluntarily hold his eye steady (typically 1 second or less). Additionally optical corneal incisions, entry cuts, and arcuate incisions, may further increase the both the time and precision requirements of a laser surgical cut.

The present disclosure aims to solve these and other challenges with an integrated ophthalmic surgical system, as described herein.

SUMMARY

In certain embodiments of the disclosure, an ophthalmic laser surgical system includes a chassis comprising a pulsed laser source configured to generate a laser beam of laser pulses and a gantry coupled to the chassis, wherein the position of the gantry with respect to the chassis is adjustable. The system further includes a reference interface coupled to the gantry. The reference interface may comprise an attachment interface configured to couple to a patient interface for docking with an eye, and the attachment interface located at a distal portion of the reference interface. Further, the reference interface may be configured to move to a first reference interface position in which the attachment interface is proximal to the chassis and a second reference interface position in which the attachment interface is distal from the chassis. The system further includes an optical head unit coupled to the reference interface. The optical head unit includes a laser scanner configured to scan the scan the laser beam of pulsed laser pulses to a target region of an eye docked to the patient interface, and a beam splitter configured to multiplex the scanned laser beam of pulsed laser pulses with an imaging beam path of an external imaging system. The optical head unit is configured to move to a first optical head unit position near a proximal end of the reference interface and a second optical head unit position which is a lockable surgical position near a distal end of the reference interface.

In certain embodiments, the reference interface is configured to move to the first reference interface position and the second reference position by extending, retracting, rotating, or swiveling. In certain embodiments, the optical head unit is configured to move to the first optical head unit position and the second optical head unit position by extending, retracting, rotating, or swiveling.

In certain embodiments, the external imaging system is an optical coherence tomography (OCT) imaging system or a surgical microscope, and the laser surgical system and the external imaging system are not rigidly coupled, such that the laser surgical system and the external imaging system vibrate independently. In certain embodiments, the external imaging system is an optical coherence tomography (OCT) imaging system or a surgical microscope, and the laser surgical system and the external imaging system are not rigidly coupled, such that a movement of the laser surgical system with respect to the external imaging system greater than an accuracy requirement for the laser surgical system.

In certain embodiments, the reference interface and optical head unit together measure no more than 300 mm vertically along an optical axis of the external imaging system when the optical head unit is in the second optical head unit position.

In certain embodiments, the attachment interface is optically aligned with the imaging beam path of the external imaging system when the reference interface is in the second reference interface position, and the beam splitter is optically aligned with the imaging beam path of the external imaging system when the optical head unit is in the second optical head unit position. In certain embodiments, the reference interface structure comprises an arm, a shelf, or a plate.

Certain embodiments further comprise a control unit communicatively coupled to the optical head unit and the external imaging system, the control unit comprising a processor configured to receive imaging data from the surgical microscope and the external imaging system, based on the received imaging data, determine a position of the eye relative to the attachment interface, and based on the determined position, control the optical head unit to scan the laser beam of pulsed laser pulses to the target region of the eye.

Certain embodiments of the disclosure comprise an ophthalmic surgical system that includes a surgical microscope configured to generate an image of an eye, and an optical coherence tomography (OCT) imaging system configured to generate an OCT image of the eye. The OCT imaging system is integrated and optically aligned with the surgical microscope. The system further includes an image capture unit configured to receive and process the images generated by the surgical microscope and the OCT imaging system and a laser surgical system that includes a chassis comprising a pulsed laser source configured to generate a laser beam of laser pulses and a gantry coupled to the chassis. The position of the gantry with respect to the chassis is adjustable.

The laser surgical system includes a reference interface structure coupled to the gantry. The reference interface comprises an attachment interface configured to couple to a patient interface for docking with an eye, and the attachment interface located at a distal portion of the reference interface. Further, the reference interface is configured to move to a first reference interface position in which the attachment interface is proximal to the chassis and a second reference interface position in which the attachment interface is distal from the chassis and is optically aligned with the imaging beam path of the surgical microscope and OCT imaging system. The laser surgical system further includes an optical head unit coupled to the reference interface. The optical head unit comprises a laser scanner configured to scan the laser beam of pulsed laser pulses to a target region of an eye docked to the patient interface and a beam splitter configured to multiplex the scanned laser beam of pulsed laser pulses with an imaging beam path of the surgical microscope and the OCT imaging system. The optical head unit is configured to move to a first optical head unit position near a proximal end of the reference interface and a second optical head unit position which is a lockable surgical position near a distal end of the reference interface.

The ophthalmic surgical system further includes a control unit communicatively coupled to the optical head unit and the image capture unit. The control unit comprises a processor configured to receive imaging data from the surgical microscope and image capture unit; based on the received imaging data, determine a position of the eye relative to the attachment interface, and based on the determined position, control the optical head unit to scan the laser beam of pulsed laser pulses to the target region of the eye.

In certain embodiments, the reference interface is configured to move to the first reference interface position and the second reference position by extending, retracting, rotating, or swiveling. In certain embodiments, the optical head unit is configured to move to the first optical head unit position and the second optical head unit position by extending, retracting, rotating, or swiveling.

In certain embodiments, the beam splitter is optically aligned with the imaging beam path of the surgical microscope and OCT imaging system when the optical head unit is in the second optical head unit position. In certain embodiments, the beam splitter is configured to multiplex the laser beam with the imaging beam path of the surgical microscope and the OCT imaging system without changing a focus or position of the surgical microscope or the OCT imaging system.

In certain embodiments, the laser surgical system and the OCT imaging system are not rigidly coupled, such that the laser surgical system and the OCT imaging system vibrate independently. In certain embodiments, the laser surgical system and the OCT imaging system are not rigidly coupled, such that movement of the laser surgical system with respect to the OCT imaging system is greater than an accuracy requirement for the laser surgical system.

In certain embodiments, the reference interface and optical head unit together measure no more than 300 mm vertically along an optical axis of the OCT imaging system when the optical head unit is in the second optical head unit position.

In certain embodiments, the optical head unit is configured to move to the second optical head unit position and cause the laser scanner to scan the laser beam of pulsed laser pulses to the target region of the eye docked to the patient interface without moving or changing a working distance of the surgical microscope or OCT imaging system. In certain embodiments, the reference interface structure comprises an arm, a shelf, or a plate. In certain embodiments, the processor of the control unit is further configured to calculate a centering, tilt and cyclo-rotation of the eye, based on the determined position of the eye relative to the attachment interface Certain embodiments provide one or more technical advantages over existing systems. For example, certain embodiments integrate surgical subsystems that are conventionally separated (often located in different surgical rooms) and combine components (e.g., OCT systems) in a novel arrangement to reduce the cost, size, and mass of the surgical system. In certain embodiments, an integrated ophthalmic surgical system may reside in a compact surgical theater and facilitate performing laser and manual surgical procedures without moving or repositioning a microscope or patient between procedures. Accordingly, certain embodiments reduce the length and cost of ophthalmic surgery. These and other advantages will be apparent to a skilled artisan in view of the present disclosure.

BRIEF DESCRIPTION OF THE DRAWINGS

For a more complete understanding of the present disclosure and the advantages thereof, reference is now made to the following description taken in conjunction with the accompanying drawings in which like reference numerals indicate like features and wherein.

Figure 1A:
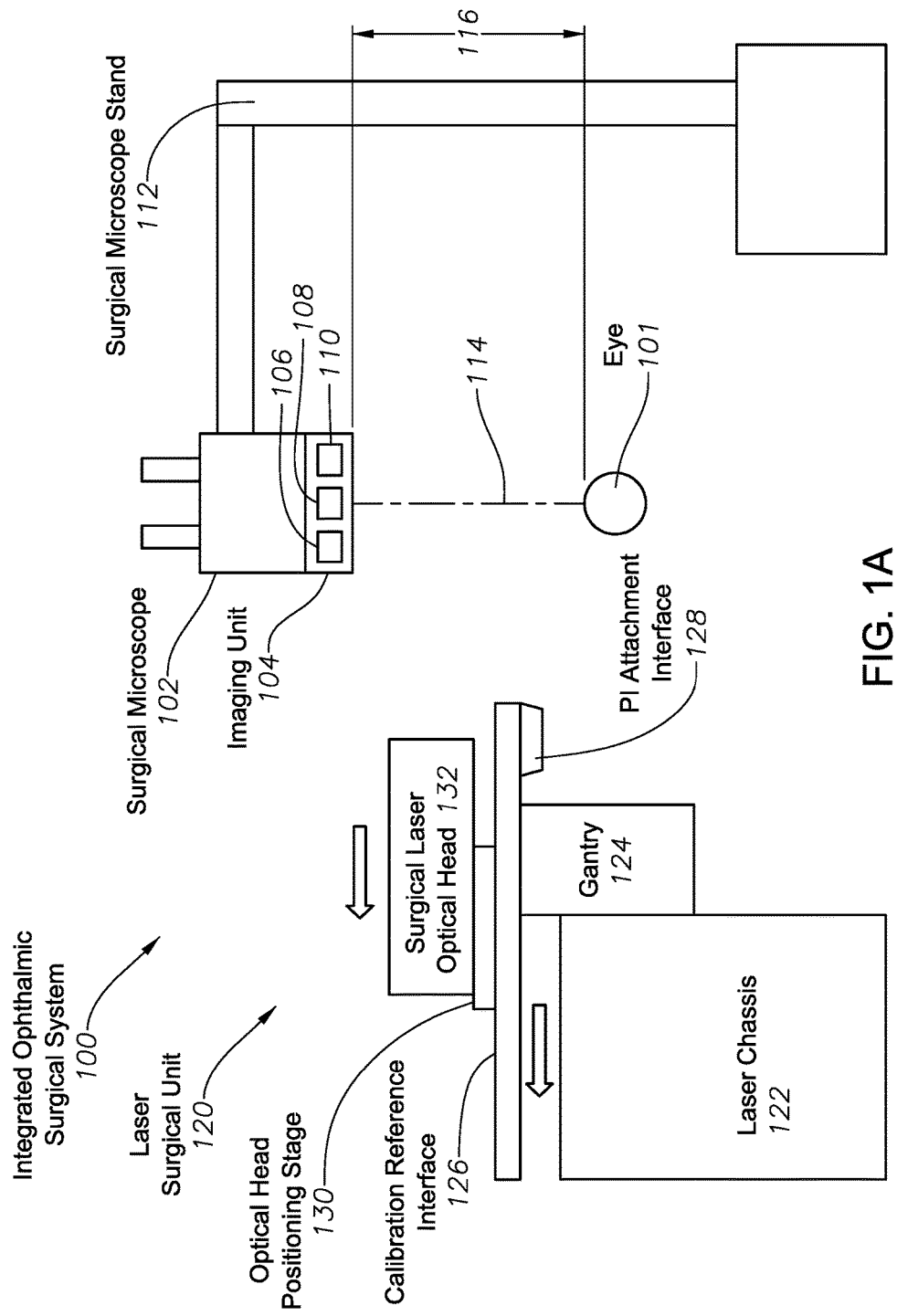
FIGS. 1A-1E and 2A-2E illustrate aspects of an integrated ophthalmic surgical system in five positions/stages, according to certain embodiments.

One skilled in the art will understand that the drawings, described below, are for illustration purposes only, and are not intended to limit the scope of applicant's disclosure.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Alterations and further modifications to the described systems, devices, and methods, and any further application of the principles of the present disclosure are contemplated as would normally occur to one skilled in the art to which the disclosure relates. In particular, it is contemplated that the systems, devices, and/or methods described with respect to one embodiment may be combined with the features, components, and/or steps described with respect to other embodiments of the present disclosure. For the sake of brevity, however, the numerous iterations of these combinations will not be described separately. For simplicity, in some instances the same reference numbers are used throughout the drawings to refer to the same or like parts.

As used herein, it should be understood that a processor may include one or more microprocessors, field-programmable gate arrays (FPGAs), controllers, or any other suitable computing devices or resources. Further, memory may take the form of volatile or non-volatile memory including, without limitation, magnetic media, optical media, random access memory (RAM), read-only memory (ROM), removable media, or any other suitable memory component. Memory may store instructions for programs and algorithms that, when executed by a processor, implement the functionality described herein with respect to any such processor, memory, or component that includes processing functionality. In addition, as used herein, components which are communicatively coupled may be configured to communicate using any suitable wired (e.g., wire, cable, fiber, etc.) or wireless (e.g., Wi-Fi, Bluetooth, NFC, IR, cellular, etc.) communications.

In general, the present disclosure relates to an integrated ophthalmic surgical system, and especially a surgical system for anterior segment surgery, such as cataract and corneal procedures. Certain embodiments include a surgical laser for anterior segment surgery integrated with a surgical microscope, an enhanced imaging device such as an optical coherence tomography (OCT) imaging unit, and an image capture device such as a video camera.

Embodiments of the present disclosure provide numerous advantages. For example, certain embodiments may improve clinical outcomes and integrate equipment used in laser and manual surgical procedures in a single, compact system. Integrated equipment and subsystems may include, for example: (1) pre-operative and/or intra-operative ophthalmic diagnostic instruments, such as an aberrometer, biometer, OCT and other devices for eye modeling, to image and measure properties of the eye and assist in eye modeling and devising a treatment plan; (2) a surgical microscope to assist the doctor with docking a surgical laser to the eye of a patient prior to a laser surgical procedure and also assist with post-laser part of the surgical procedure, cataract removal, and intra-ocular lens placement; (3) an OCT instrument for capturing detailed anatomical features of the tissues inside the eye and provide targeting locations for the surgical laser, as well as providing further diagnostic information of the eye assisting the doctor in selecting intra-ocular lenses for cataract surgery after the laser portion of the surgery is complete; (4) an image capture device, such as a high resolution CCD or CMOS camera in a normal or Scheimpflug arrangement, for capturing anatomical features of the outside of the eye, tracking eye features and movements, and providing targeting locations for the surgical laser referenced to pre-operative diagnostic information; (5) an ophthalmic surgical laser, such as a femtosecond laser and associated optics, for making laser incisions in ophthalmic tissue according to treatment plan; and (6) one or more display units for projecting visual images into the view of the microscope or onto a heads-up display. In certain embodiments, surgical equipment and subsystems may be physically integrated and/or virtually communicatively integrated via data connectivity.

FIGS. 1A-E and 2A-E illustrate examples of an integrated ophthalmic surgical system according to particular embodiments of the present disclosure. FIGS. 1A-E and 2A-E are not drawn to scale, and one skilled in the art will appreciate that system 100 includes additional components that are not illustrated herein for the sake of simplicity.

Integrated ophthalmic surgical system 100 includes a surgical microscope 102, an imaging unit 104, and a laser surgical unit 120, the components of which are communicatively coupled to one another via wired or wireless communication. A control unit comprising a processor and memory (not shown) may be communicatively coupled to each component of system 100 to facilitate electronic communication between and operation of such components, and receive and respond to user inputs. Certain embodiments may include additional components and subsystems, including diagnostic instruments (e.g., aberrometer, biometer, Swept-source OCT, etc.) to assist a surgeon in devising a treatment plan preoperatively, assessing a patient intraoperatively, or otherwise providing surgical guidance.

Surgical microscope 102 may facilitate magnified viewing of a patient's eye 101 during a surgical procedure and may generally include eyepieces, a relay lens, magnifying/focusing optics, an objective lens, and surgical viewing optics. Surgical microscope 102 may include any suitable optical or electronic components for providing a view of a patient's eye to the surgeon. In certain embodiments, surgical microscope 102 comprises a high resolution, high contrast stereo viewing surgical microscope. One example of a surgical microscope 102 is the LuxOR™ LX3 with Q-VUE™ Ophthalmic Microscope, available from Alcon. Surgical microscope 102 may assist a surgeon with docking a surgical laser to the eye of a patient prior to a laser surgical procedure. Surgical microscope 100 may also be used by the surgeon during a manual procedure, for example to manually create an incision, remove a cataract, or insert and position an intra-ocular lens. In certain embodiments, surgical microscope 102 may be communicatively coupled to other components of system 100, such as laser optical head 132, components of imaging unit 104, and a controlling unit.

Mounted on surgical microscope 102 is an imaging unit 104, which includes OCT system 106, image capture system 108, and display system 110. OCT system 106, image capture system 108, and display system 110 may be communicatively coupled to each other, and to optical laser head 132 and a controlling unit. In certain embodiments, the components of imaging unit 104 may be fully integrated with surgical microscope 102 and reside in a unified housing.

OCT system 106 may include a light source, a beam scanner, an imaging arm, and a reference arm. In general, the light source may generate an OCT imaging beam, and the beam scanner may direct a portion of the OCT imaging beam to a particular region within the patient's eye 101 via an imaging arm, and a portion of the OCT imaging beam to the reference arm. Reflections of the OCT imaging beam from the particular region within the patient's eye 101 may return to the OCT system 106 along the same optical path as the imaging beam, and system 106 may generate OCT images of the particular region by determining interference between the reflections received by the imaging arm and reflections received by the reference arm. OCT system 106 may include a processor, memory, and additional components (not shown) for manipulating the OCT imaging beam and generating 2D or 3D OCT images. In certain embodiments, OCT system 106 may be a swept-source OCT system or a spectral-domain OCT system.

OCT imaging system 106 may be operable to generate live (real-time) OCT images of the patient's eye 101 and communicate those images to other components of system 100. OCT imaging system 106 may capture detailed anatomical features of the tissues inside eye 101 and provide targeting locations for laser surgical unit 120, as well as provide diagnostic information to assist a surgeon during manual stages of an anterior segment procedure. For example, OCT imaging system 106 may assist a surgeon in selecting, inserting, and positioning IOLs after the laser portion of the surgery is complete.

Although the embodiments depicted in FIGS. 1-4 depict an OCT system 106, other embodiments of the disclosure may use alternative depth-resolved imaging systems, such as ultrasound or photoacoustic imaging systems.

Image capture system 108 may capture anatomical features of the outside of eye 101 and provide targeting locations for laser surgical unit 120 referenced to preoperative diagnostic information. Image capture system 108 may include magnification and focusing optics, and may comprise one or more digital video cameras, line scan ophthalmoscopes or confocal-scanning ophthalmoscopes. In certain embodiments, image capture system 108 comprises a high resolution CCD or CMOS camera in a normal or Scheimpflug arrangement. Image capture system 108 may include a processor and memory configured to process image data. For example, image capture system 108 may comprise a processor configured to execute feature detection and/or eye tracking algorithms to identify features of eye 101 within an image and, based on an analysis of image data, generate visual indicator overlays for display to a surgeon via display system 100. For example, image capture system 108 may generate overlays to assist a surgeon with the location of incisions, IOL positioning, and toric alignment. In certain embodiments, image capture system 108 may receive image data from surgical microscope 102 or OCT system 106 to generate images of patient's eye 101. Image capture system 108

Display system 110 receives images and surgical data from other components of system 100, such as surgical microscope 102, OCT system 106, image capture system 108, and laser surgical unit 120, and displays such data to a user. In certain embodiments, display system 110 may output display data to one or more heads-up monitors in surgical system 100, or a real-time data projection system configured to display images and data surgeon via a display screen or eyepieces of microscope 102. Display system 110 may include a processor, memory, and any suitable components for generating visual displays, as understood by those skilled in the art.

Surgical microscope 102 is physically coupled to surgical microscope stand 112. Microscope stand 112 supports and facilitates positioning of surgical microscope 102 and imaging unit 104 in three dimensions to align with patient's eye 101 before and during an ophthalmic surgical procedure. The position of microscope stand 112 may be lockable, and movements of microscope stand 112 may be performed manually or by stepper motors, servo motors or similar electro-mechanical actuators at the direction of a control unit of system 100.

A control unit of system 100 (not shown) may be communicatively coupled to surgical microscope 102, OCT system 106, image capture system 108, display system 100, laser surgical unit 120, and other components of system 100 to facilitate electronic communication between such subsystems. The control unit may include a processor and memory configured to provide the functionality described herein. For example, the control unit may be programmed to (or may store software in memory that, when executed by a processor, is operable to) obtain and store preloaded surgical and diagnostic data, receive and store images and data obtained in real time by surgical microscope 102, OCT system 106, image capture system 108, or other components of system 100, and process received images and data to output information for display to a surgeon or control components of surgical microscope 102, imaging unit 104, or laser surgical unit 120. In certain embodiments, the control unit may perform calibration calculations and procedures among components of system 100. In certain embodiments, the control unit may be an imaging-based laser controller configured to control components of surgical laser optical head unit 132 (e.g., scanners 206 and 208) to direct a laser beam to specific tissues of eye 101, based on received image data and calculations performed by the control unit. The control unit may be a standalone component of system 100, or may be integrated and/or housed with other components of system 100 in any suitable manner. In certain embodiments, the control unit may be located in surgical laser optical head 132, laser chassis 122, or imaging unit 104, or may be mounted to surgical microscope 102 or microscope stand 112. In certain embodiments, multiple communicatively-coupled processor modules located in different subsystems of system 100 may work together to provide the functionality of a control unit described herein.

System 100 further includes laser surgical unit 120, which comprises laser chassis 122, gantry 124, calibration reference interface 126, PI attachment interface 128, positioning stage 130, and laser optical head 132 coupled as shown in FIGS. 1A-E and 2A-E. In FIGS. 2A-E, laser surgical unit 120 is coupled to surgical microscope stand 112. Laser surgical unit 120, laser chassis 122, gantry 124, calibration reference interface 126, PI attachment interface 128, positioning stage 130, and laser optical head 132 may include features and components (not expressly discussed herein for simplicity) to facilitate generation and delivery of a pulsed laser beam to an ophthalmic target. Aspects of surgical laser systems for anterior segment surgery are described in U.S. Pat. Nos. 8,414,564, 8,419,721, 8,500,725, 8,506,559, 8,764,737, 8,908,739, 8,920,407, 9,044,303, and 9,054,479, which are incorporated by reference herein in their entirety.

Laser chassis 122 comprises a pulsed laser source for generating laser pulses to be directed towards eye 101 by laser optical head 132. In certain embodiments, laser chassis comprises a femtosecond laser engine capable of generating laser pulses at or below 800 fs at approximately 1030 nm wavelengths, with less than 20 µJ pulse energy and variable repetition rates between 50-500 kHz. The laser engine may comprise a chirped-pulse amplification (CPA) laser architecture utilizing a femtosecond oscillator, pulse stretcher, optical amplifier, and pulse compressor. In certain embodiments, the oscillator may produce either femtosecond pulses or slightly stretched (chirped) pulses (1-5 ps) that are compressible to femtosecond pulse lengths. Direct optical amplification of such short pulses to required pulse energies is not practical because high optical peak power would lead to the damage of the amplifier. Therefore, prior to amplification, pulses may be stretched in time by a pulse stretcher. Pulse duration may be increased by 100-1000 times and peak powers are proportionally reduced. This allows amplification of pulses to the required pulse energies without damage. After amplification, pulses may be compressed back to the femtosecond durations by the pulse compressor. The net dispersion of the CPA laser should approach zero, therefore dispersion of individual modules and components need to be carefully managed, including higher order dispersion terms beyond group velocity dispersion (GVD). The laser engine in laser chassis 122 may utilize a bulk (freespace), fiber, or hybrid design. In bulk designs, light mostly propagates through the laser as beams in free space (air). In fiber lasers, light is mostly confined within optical fibers and therefore fiber lasers are often referred to as integrated lasers. Hybrid lasers use a combination of bulk and fiber modules. Laser chassis 122 may include any suitable components for generating a surgical laser beam as understood by those of skilled in the art.

Gantry 124 is adjustably coupled to laser chassis 122. Gantry 124 supports and facilitates positioning of calibration reference interface 126 and PI attachment interface 128 in three dimensions. Gantry 124 may include an assembly of translation and/or rotation stages to extend, retract, rotate, swivel, or otherwise move calibration reference interface 126 and PI attachment interface 128 into position to dock with a patient's eye, or withdraw to provide room for a manual procedure. Gantry 124 may provide lockable positions to secure the position of calibration reference interfaced 126 and PI attachment interface 128. Movements of gantry 124 may be performed manually or by stepper motors, servo motors or similar electro-mechanical actuators under the control of a control unit of system 100. Additionally, the translation and/or rotation stages of gantry 124 may be weight balanced and vertically floating to provide a safety buffer and limit the force exerted on the eye during docking.

Calibration reference interface 126 is coupled to gantry 124 and configured to facilitate positioning of PI attachment interface 128 and provide a reference for laser optical head 132. The gantry 124 and the calibration reference interface 126 are constructed in a way that together they provide movement in 3 degrees of freedom, to facilitate positioning the PI attachment interface 128 onto the eye. In certain embodiments, gantry 124 may be configured for linear movements in the horizontal x and vertical z direction while the calibration reference interface is configured for linear movement in the horizontal y direction, orthogonal to x and z. In other embodiments (see, e.g., FIGS. 2A-E) calibration reference interface 126 is configured for rotational movement $\phi$ around a vertical axis, and coordinated movements along x, z and $\phi$ facilitates positioning the PI attachment interface 128 onto the eye. Movements along the x, y, z and $\phi$ coordinates may be manual or motorized. In certain embodiments, calibration reference interface 126 may comprise a plate, shelf, beam, mechanical arm, or other structure. Calibration reference interface 126 may be constructed according to designs and using materials which permit it to be relatively thin (e.g., 5-20 mm thick) yet rigid throughout all positions of system 100 (e.g., positions shown in FIGS. 1A-E and 2A-E). For example, calibration reference interface 126 may be rigidly constructed such that the movement of optical head positioning stage 130 and laser optical head 132 from the calibration positions shown in FIGS. 1C and 2C to the surgical positions shown in FIGS. 1D and 2D does not cause movement at the distal end of optical head positioning stage 130, in order to preserve the validity of the calibration. Calibration reference interface 126 may be constructed of aluminum, titanium, carbon fiber, plastic, or any suitable material.

Calibration reference interface 126 may include an opening or aperture near a distal end to allow imaging beams and laser beams generated by components of system 100 to pass through to eye 101, and may further include one or more reference features or marks near or in the opening or aperture (e.g., target signs, cross hairs, scales, etc.) to assist with feature recognition in images obtained by imaging unit 108 and/or surgical microscope 102. Calibration reference interface 126 may provide a mechanical reference to a patient's eye and may be used as an intermediate reference point. For example, rather than directly calibrating a patient's eye to a surgical laser (in terms of mechanical position), certain embodiments of system 100 may calibrate the eye to calibration reference interface 126, and then reference calibration reference interface 126 to the surgical laser.

Figure 3:
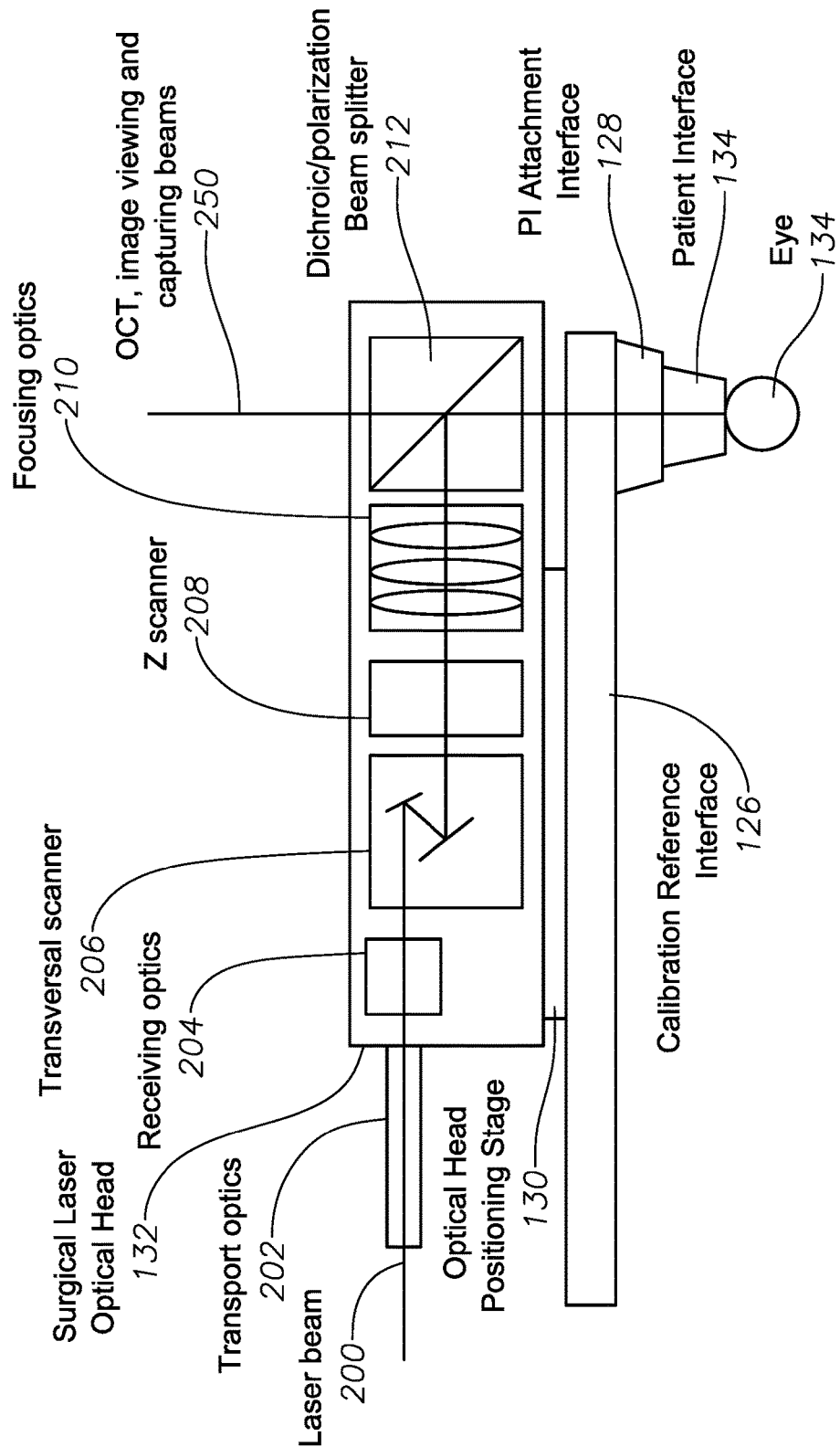
FIG. 3 illustrates aspects of a surgical laser unit in additional detail, according to certain embodiments.
Figure 4:
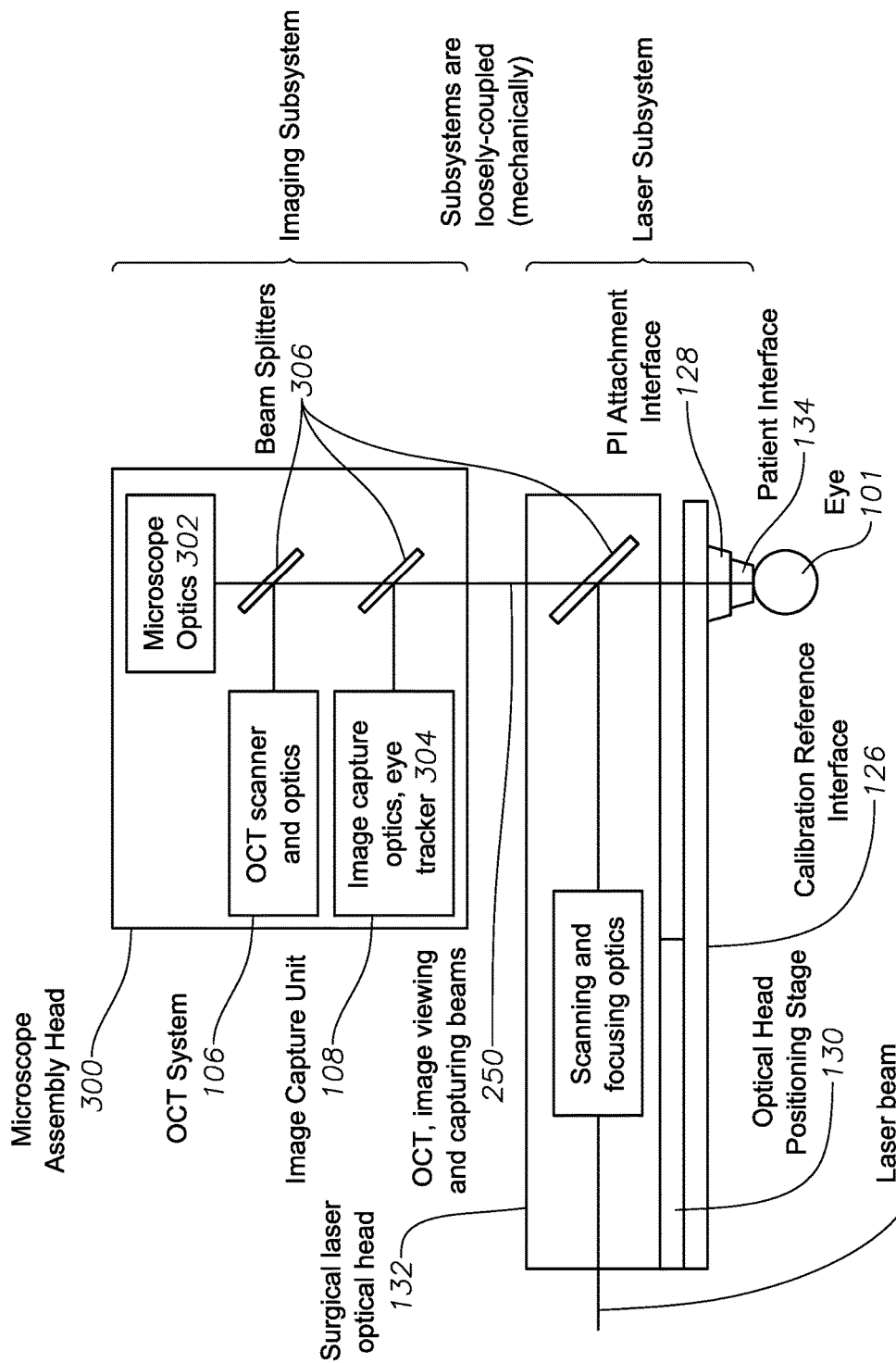
FIG. 4 illustrates aspects of an imaging subsystem and laser subsystem in additional detail, according to certain embodiments.

Calibration reference interface 126 may be adjustably positioned with respect to laser chassis 122 via gantry 124. For example, in a first position calibration reference interface 126 may be retracted, rotated, or otherwise moved such that its distal end is withdrawn to a position proximal to chassis 122 for a pre-diagnostic or manual surgical procedure (e.g., FIGS. 1A, 2A, 1E, 2E). Calibration reference interface 126 may also be extended, rotated, or otherwise moved to a second position in which its distal end is distal from chassis 122, and positioned within the beam path 114 of surgical microscope 102 and imaging unit 104 (e.g., FIGS. 1B-1D, 2B-2D). When calibration reference interface 126 is moved to the second position for calibration or a laser surgical procedure, the opening or aperture may be optically aligned with the imaging beam path of surgical microscope 102, OCT system 106, and image capture system 108, such that the imaging beams may pass through the opening or aperture to eye 101, as shown in FIGS. 3 and 4. In various embodiments, calibration reference interface 126 may be arranged in intermediate positions between the first and second position, and the positions may be lockable. Movements of calibration reference interface 126 may be performed manually or by stepper motors, servo motors or similar electro-mechanical actuators under the control of a control unit of system 100.

PI attachment interface 128 may be located at a distal end of calibration reference interface 126 and may be configured to receive a patient interface 134 for mechanically docking to eye 101. In certain embodiments, PI attachment interface 128 is configured to receive a disposable patient interface 134 that includes a contact lens and suction ring which may be lowered onto eye 101 to immobilize it during a laser surgical procedure. In various embodiments, PI attachment interface 128 may receive or otherwise attached to a one piece or multi-piece patient interface 134 which may be initially attached to either eye 101 or attachment interface 128. PI attachment interface 128 may be designed to accommodate any suitable types or types of patient interface 134. Aspects of example patient interfaces and PI attachment interfaces for use with an ophthalmic surgical laser are described in U.S. Pub. Nos. 2009/0069794 and 2014/0216468, and U.S. Pat. Nos. 8,845,624, 8,939,967, 9,089,401, and 9,044,304, which are fully incorporated by reference herein. PI attachment interface 128 may be constructed of aluminum, titanium, carbon fiber, plastic, or any suitable material, and may be attached to or integrated with calibration reference interface 126.

Positioning stage 130 is coupled to calibration reference interface 126 and laser optical head 132. Positioning stage 130 facilitates positioning laser optical head 132 at different locations, and may comprise one or more translation and/or rotation stages. In certain embodiments, positioning stage 130 comprises a weight balanced, vertically floating stage configured to limit the force exerted on eye 101 during docking and at the docked stage. Positioning stage 130 may also act as a safety buffer to give range and minimize the forces on eye 101 during occasional movements of the patient or the surgical bed when docked to laser surgical unit 120.

In certain embodiments, laser optical head 132 is mounted on optical head positioning stage 126, which is configured to extend, retract, rotate, hinge, and/or swivel to pre-determined stop locations relative to calibration reference interface 126. Such stop locations may be determined by mechanical hard stops, position encoders, or other suitable mechanism. In certain embodiments, positioning stage 130 may be configured to move optical head unit 132 to a first position near a proximal end of reference interface 126, withdrawn toward chassis 122 (e.g., FIGS. 1B-C, 2B-C). Positioning stage 130 may also be configured to move optical head unit 132 to a lockable surgical position near distal end of reference interface near PI attachment interface 128 (e.g., FIGS. 1D, 2D). In the surgical position, a dichroic/polarization beam splitter 212 of optical head unit 132 may be optically aligned to multiplex a scanned laser beam 200 with the imaging beams generated by surgical microscope 102, OCT system 106, and image capture system 108, as shown in FIGS. 3 and 4. Movements of positioning stage 130 to position laser optical head 132 and positioning stage 130 may be performed manually by an operator or by one or more stepper motors, servo motors or other electro-mechanical actuators under the direction of a control unit.

Positioning stage 130 and calibration reference interface 126 may be rigidly constructed to support the weight of surgical laser optical head 132 in various positions, including the surgical position, without flexion or movement in any direction to preserve the validity of calculated calibrations without regard to the position of laser optical head 132.

Laser optical head 132 delivers laser pulses from the laser engine housed in laser chassis 122 to target locations within eye 101 with requisite position accuracy, focal spot quality, and speed. Laser optical head 132 connects optically to the laser engine via beam transportation optics (not shown) such as an articulating arm or optical fiber, and may include a receiver or beam conditioner optics for the laser light, a three-dimensional laser scanner and focusing optics. In addition, laser optical head 132 may include a dichroic or polarization beam splitter to multiplex a scanned laser beam with one or more imaging beams of surgical microscope 102 and components of imaging unit 104. This may allow the surgeon and the controller to observe target tissues and select treatment location and treatment patterns. An optional eye tracker can be used to assist target selection. Additional calibrations and tissue referencing to pre-operational images and diagnostic data can also be performed at this stage, just prior to laser treatment. Components of laser optical head 132 are depicted in additional detail in FIG. 3.

FIGS. 1A-E and 2A-E illustrate embodiments of system 100 in five stages or positions. FIGS. 1A-E illustrate an embodiment of integrated ophthalmic surgical system 100 in which laser surgical unit 120 is communicatively, but not physically, coupled with surgical microscope stand 112, surgical microscope 102, or imaging unit 104. In FIGS. 2A-2E, laser surgical unit 120 is both communicatively and physically coupled with surgical microscope stand 112, surgical microscope 102, and imaging unit 104.

Figure 2A:
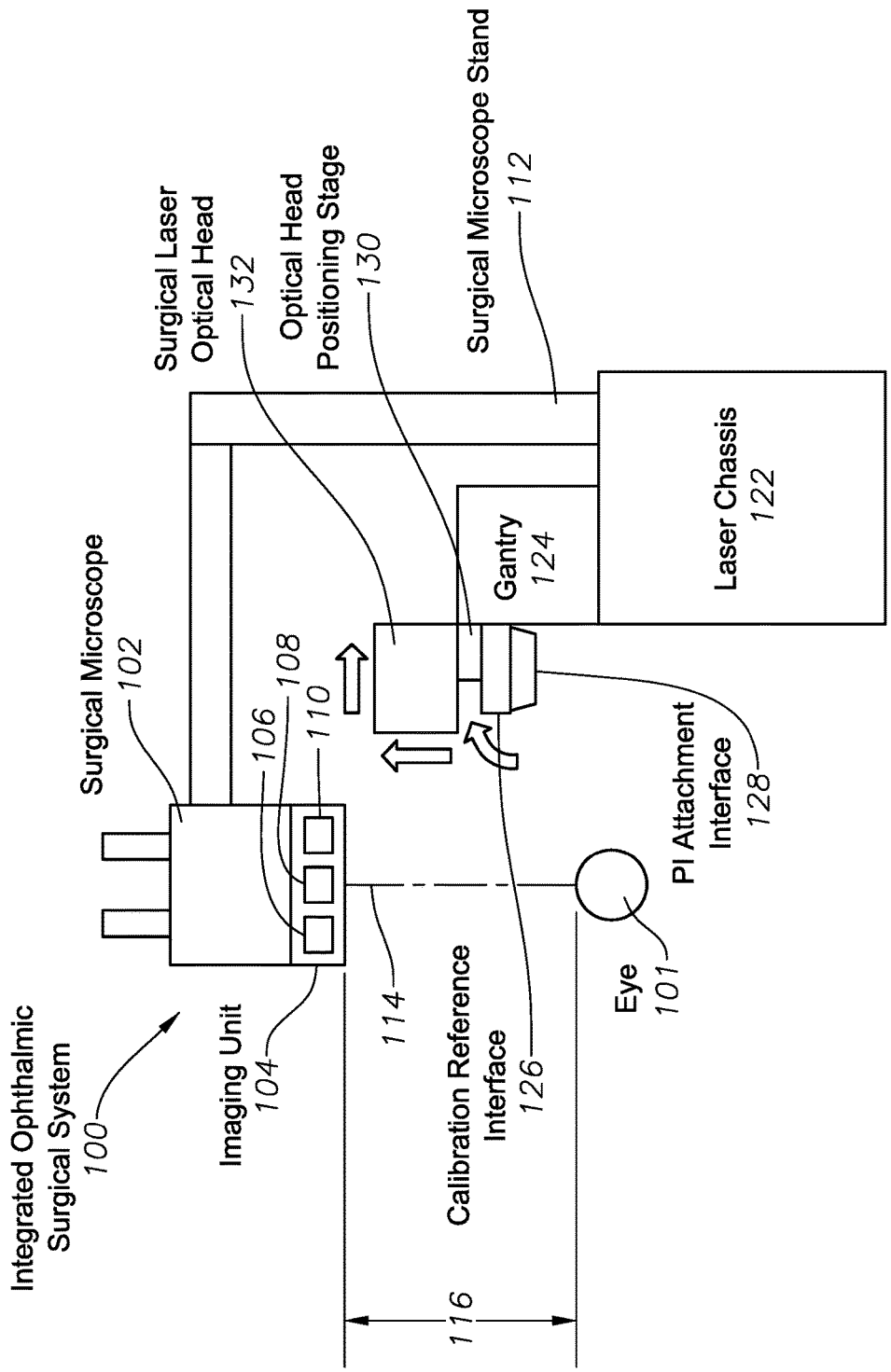

FIGS. 1A and 2A illustrate system 100 arranged in a preoperative diagnostic position. In FIGS. 1A and 2A, surgical microscope 102 and imaging unit 104 are positioned and aligned with respect to eye 101. To facilitate imaging of eye 101, a beam path 114 coinciding with the optical axis of surgical microscope 102 and imaging unit 104 is directed toward eye 101, and positioned at a working distance 116 from eye 101. The relative position of eye 101, surgical microscope 102, imaging unit 104 are typically arranged to suit the surgeon's space needs for performing a manual portion of the surgical procedure. A typical working distance may be between approximately 150 and 300 mm.

At this stage the operator can set the focus and magnification of the surgical microscope 102 to his/her preferred settings, and diagnostic procedures may be performed.

In FIGS. 1A and 2A, components of laser surgical unit 120 are shown arranged in a standby position. In particular, calibration reference interface 126 and positioning stage 130 are in a fully withdrawn position, as indicated by the arrows, to avoid interfering with positioning the patient and microscope. Positioning to the withdrawn position may be facilitated by translation and/or rotation stages of gantry 124 and positioning stage 130.

Figure 1B:
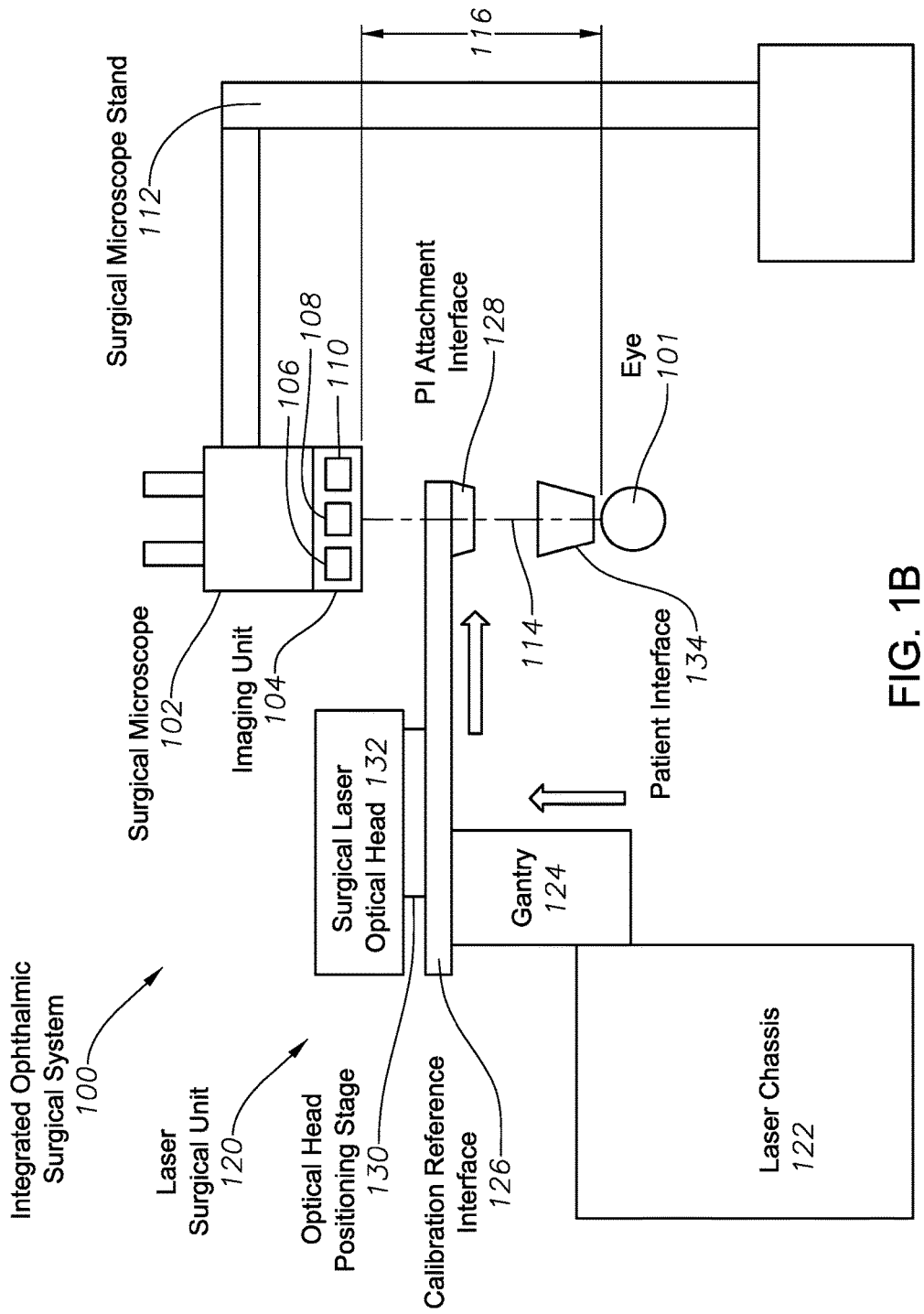
Figure 2B:
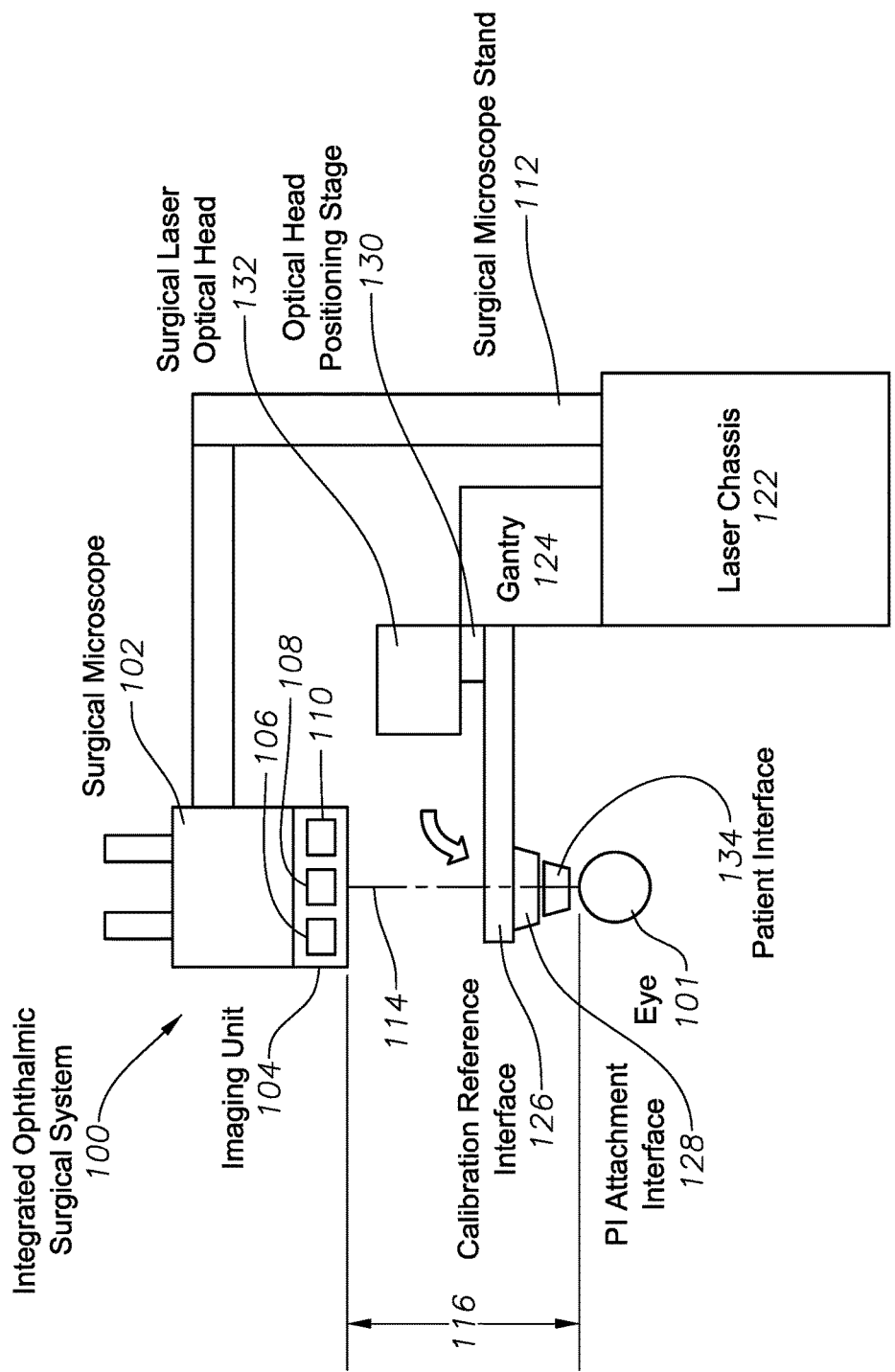

FIGS. 1B and 2B illustrate system 100 arranged in a pre-docking position for preparing to dock to eye 101. In this position, positioning stage 130 (and thus surgical optical head 132) remains withdrawn to avoid interfering with the optical path 114 of surgical microscope 102 and imaging unit 104. Calibration reference interface 126, however, is positioned (either manually or under the direction of the control unit) between eye 101 and surgical microscope 102/imaging unit 104, within optical path 114. FIG. 1B illustrates an example in which calibration reference interface 128 may move laterally to extend away from gantry 124 and laser chassis 122, as indicated by the arrow. FIG. 2B illustrates an example in which calibration reference interface 128 may move rotationally such that a proximal end pivots away from gantry 124 and laser chassis 122, as indicated by the arrow.

Initially, calibration reference interface 126, which may be a thin, rigid plate or arm, may be positioned approximately midway along optical path 114 to provide sufficient room for the patient and patient interface 134. Patient interface 134 may be positioned to couple with eye 101 and PI attachment interface 128. Patient interface 134 may be initially attached either to eye 101 or PI attachment interface 128; in the case of a multi-piece patient interface 134, one part may be initially attached to eye 101 and another part may be initially attached to PI attachment interface 128.

Figure 1C:
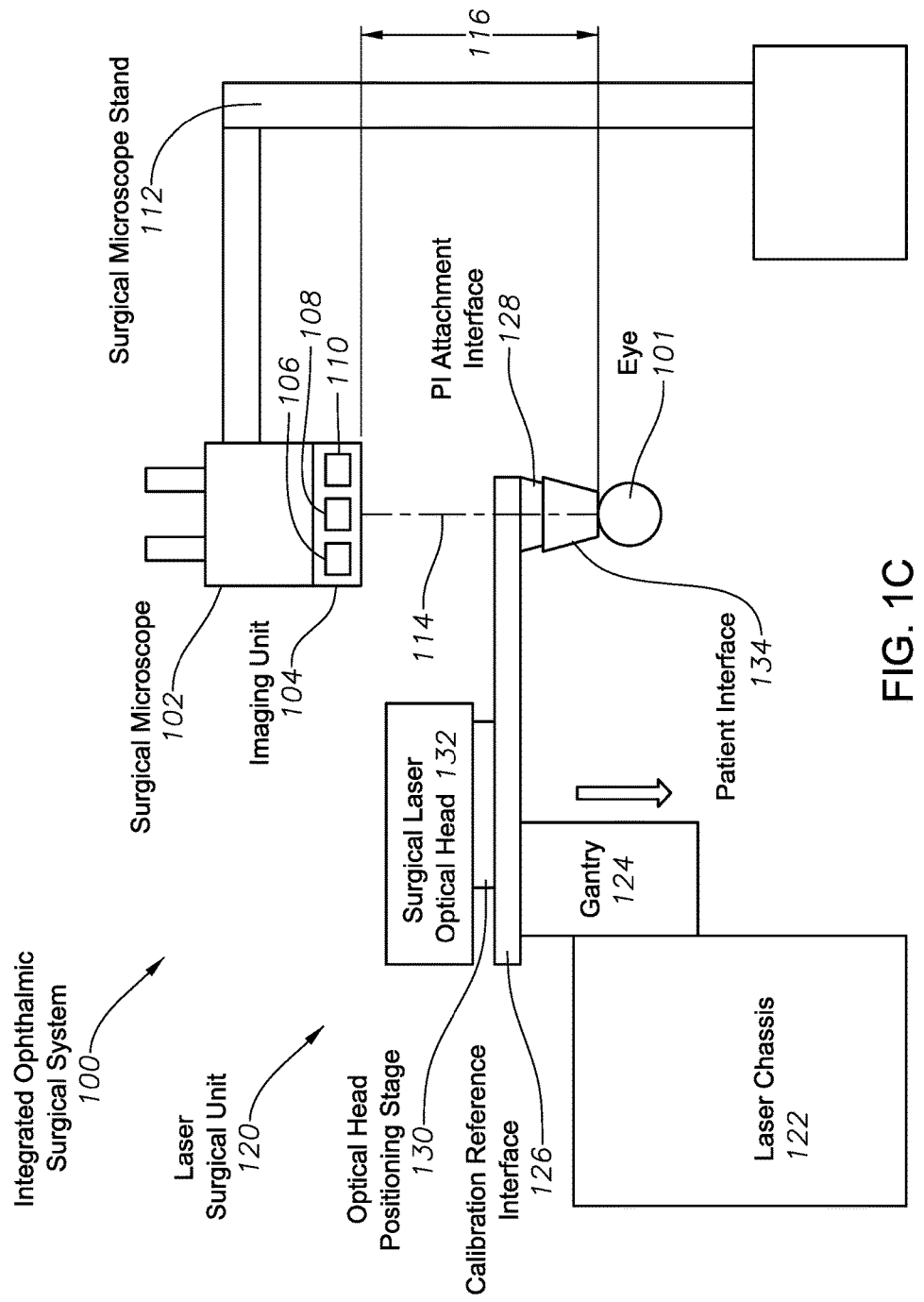
Figure 2C:
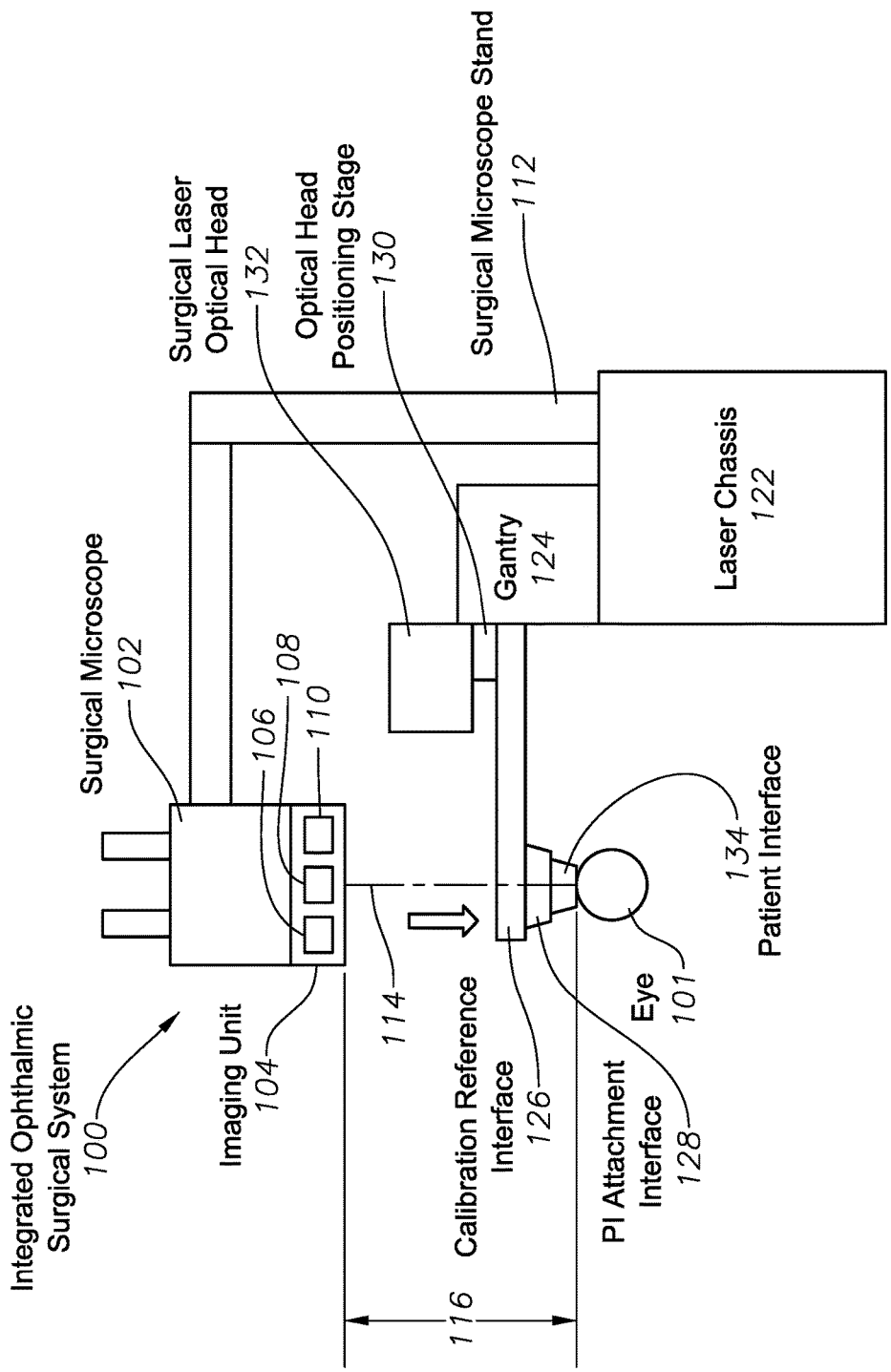

FIGS. 1C and 2C illustrate system 100 arranged in a docked calibration position, such that patient interface 134 is attached to PI attachment interface 128 and docked to eye 101. As these figures illustrate, calibration reference interface 126 may be carefully lowered and positioned (manually or under the direction of the control unit) so that PI attachment interface 128, patient interface 134, and eye 101 are in contact and eye 101 is immobilized using, for example a suction ring or other device on interface 134. To control and limit force exerted on eye 101 during docking and while docked, positioning stage 130 may comprise a weight balanced, vertically floating stage supporting laser optical head 132. Positioning stage 130 may also be designed with a flexible safety buffer to provide limited range of movement and minimize forces exerted on the eye during occasional movements of the patient or the surgical bed when docked.

In certain embodiments, such as those depicted in FIGS. 1A-1E, imaging unit 104 is attached to surgical microscope 102, both of which are supported by surgical microscope stand 122. Neither imaging unit 104 nor surgical microscope 102 is physically coupled to eye 101 or laser surgical unit 120. In embodiments depicted in FIGS. 2A-E, laser chassis 122 is coupled to surgical microscope stand 122, which supports surgical microscope 102 and imaging unit 104. However, in both arrangements, although imaging unit 104 and surgical microscope 102 may appear to be essentially stationary, they may not be considered rigidly attached to laser surgical unit 120 or eye 101. This is because stand-alone surgical microscopes mounted on a microscope stand via an arm, even when untouched, tend to vibrate or oscillate at a low frequency (e.g., approximately 1 Hz) with an amplitude larger than the required position accuracy of the laser optical head 132 (e.g., approximately 10-50 µm). Thus, in embodiments depicted in FIGS. 1 and 2, laser surgical unit 120 may thus be considered "loosely coupled" to OCT system 106, image capture system 108, and other components of system 100 from a mechanical perspective. In such embodiments, it may be necessary to calibrate subsystems in system 100. For example, it may be necessary to calibrate laser surgical unit 120 to OCT system 106 and image capture system 108 to precisely position a surgical laser incision in eye 101, in light of the relative movement of the subsystems.

Certain calibrations among components of system 100 may be performed in advance at the factory or prior to docking the patient (without the presence of eye 101). For example, in embodiments in which OCT system 106 and image capture unit 108 are housed together and rigidly coupled, determination of magnification scale factors and overlapping OCT and visual image reference frames can be performed at the factory. Likewise, magnification scale factors between the laser optical head 132 and OCT system 106 and image capture unit 108 can be performed in the factory, since these factors are affected only by the distance of the subsystems to the eye, which may be either pre-determined or set at the time of surgery. The distance of OCT system 106 and image capture unit 108 unit to eye 101 can be preferably set during the first phase (FIGS. 1A, 1B), re-measured, and verified at this third phase (FIGS. 1C, 2C).

However, other calibrations, such as centering, tilt and cyclo-rotation of the eye, must be performed with the eye present. The position illustrated in FIGS. 1C and 2C may advantageously facilitate such calibrations, without positioning laser optical head 132 within beam path 114. In other embodiments, calibration may be performed in the surgical position illustrated in FIGS. 1D and 2D.

Requisite calibrations may be determined using calibration reference interface 126 as a reference object. In particular, calibration reference interface 126 may be extended, rotated, or otherwise moved into a surgical position within beam path 114 such that other components of the system, such as OCT system 106 and image capture unit 108, may image eye 101 through calibration reference interface 126 to establish reference points that may be used to calculate coordinates to precisely scan a laser beam to target tissue during a surgical procedure. In certain embodiments, the control unit of system 100 may receive image data from OCT system 106 or image capture system 108, and may execute instructions to identify reference points of calibration reference interface 126 with respect to eye 101. Based on identified reference points (e.g., a position of one or more landmarks associated with eye 101, such as a position of the iris, position of the pupil, apex of the anterior capsule, apex of the posterior capsule, apex of the cornea, etc.), the control unit may perform measurements, generate an eye model for eye 101, and calculate and store values for calibration variables corresponding to de-centering, tilt and cyclo-rotation of eye 101 relative to calibration reference interface 126. Such values may be sent to laser surgical unit 120 and used to precisely position a surgical incision, or may be used by the control unit to direct the laser surgical unit. In certain embodiments, calculated calibration values received by the control unit, which uses them as inputs to generate a laser scanning pattern to direct the laser surgical units.

For example, to calibrate laser optical head 132 with image capture system 108, the control unit may receive one or more reference image frames of eye 101, with calibration reference interface 126 in view within the reference images, from image capture system 108. A control unit of system 100 may analyze received reference images and execute a feature recognition algorithm (e.g., edge detection, corner detection, blob detection, blob extraction, ridge detection, scale-invariant feature transform, motion detection, background subtraction, frame difference, optical flow, thresholding, template matching, Hough transform, etc.) to identify the position of landmarks in eye 101 and/or features of reference interface 126 and, based on the calculated positions, calculate a position and rotation angle (e.g., de-centering, tilt, cyclo-rotation) of eye 101 relative to calibration reference interface 126 (or features thereof). As noted above, calibration reference interface 126 may include one or more reference features such as target signs, cross hairs, scales, etc. arranged to appear within a reference image to assist the feature recognition process. The control unit may generate a reference coordinate frame to be provided to laser optical head 132, enabling laser optical head 132 to precisely position surgical incisions in eye 101. Additionally or alternatively, the control unit may direct laser optical head 132 and precisely position a surgical incision based on calculated values. Such calibration processes may ensure that image capture system 108 and laser optical head 132 are aligned lateral to an optical axis of imaging unit 104 (i.e., calibrated in the x-y direction). Acquiring and analyzing reference images may take only a few milliseconds (or less).

It may further be necessary to calibrate laser optical head 132 to OCT system 108 in three reference dimensions (e.g., in the x-y-z direction) in order to, for example, position a surgical incision at precise z-depths along an optical axis within eye 101 to perform a capsulorhexis or lens fragmentation procedure (e.g., between 3-8 mm) or a corneal flap incision (e.g., <1 mm). In embodiments in which the relative position of OCT system 106 and image capture system 108 does not change (e.g., they are housed in the same mechanical housing attached to microscope 102), the lateral or x-y calibration of OCT system 106 to image capture system 108 may be performed at the factory or clinical site without the presence of an eye. An example of such a calibration technique which uses simultaneous imaging of pre-fabricated target patterns is described in U.S. Pat. No. 8,764,737, which is incorporated by reference herein in its entirety.

Once OCT system 106 is laterally (x-y) calibrated to image capture system 108, and image capture system 108 is laterally calibrated to laser optical head 132 (as described above), lateral calibration of OCT system 106 to laser optical head 132 is a straightforward numerical calculation which may be performed and stored by the control unit.

Further, movement errors during depth calibration (along the optical axis) of OCT system 106 can be reduced or eliminated by positioning a return mirror of the reference arm of OCT system 106 on a fixture which is stationary relative to calibration reference interface 126 and eye 101. Accordingly, in certain embodiments calibration reference interface 126 (or, in certain embodiments, laser optical head unit 132) comprises a mirror, lens, or other reflective target near the opening or aperture (at the distal end) which is optically aligned to an imaging beam path of a reference arm of OCT system 106 (housed in imaging unit 104) when calibration reference interface 126 is in a docked calibration position or surgical position, as shown in FIGS. 1C-D and 2C-D. With such an arrangement, during movement between OCT system 106 and the calibration target of eye 101, changes of optical path lengths for the imaging arm and the reference arm of OCT system 106 occur simultaneously offset or cancel out one another. Typically, slight movement of OCT system 106 will not affect calibration or measurement, which may be performed as described in U.S. Pat. No. 8,764,737, or according to any suitable technique.

Accordingly, laser optical head 132 can utilize image data generated by OCT system 106 and image capture unit 108, which are microscope-mounted for use during a manual part of a surgical procedure and are not rigidly coupled to laser optical head 132. This aspect of the disclosure allows laser surgical unit 120 to utilize microscope-mounted OCT system 106 and image capture system 108, rather than separate, dedicated OCT and image capture systems. Thus, certain embodiments may reduce or eliminate electromagnetic (including optical) interference caused by two OCT systems running in parallel, may reduce the cost of surgical equipment by eliminating the need for an OCT system dedicated to the laser unit, and may reduce the mass of laser surgical unit 120 to facilitate safer docking to a patient's eye.

Figure 1D:
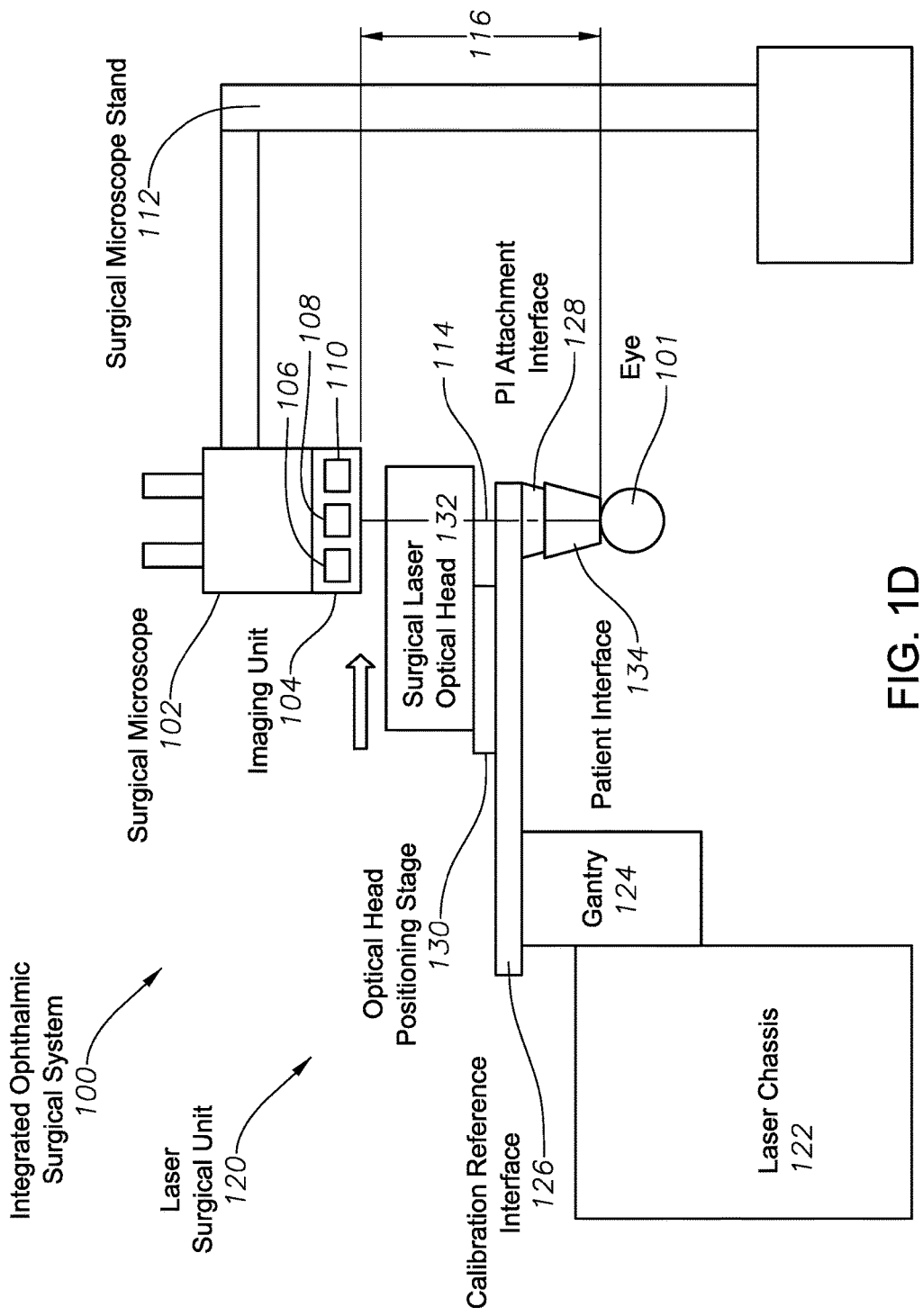
Figure 2D:
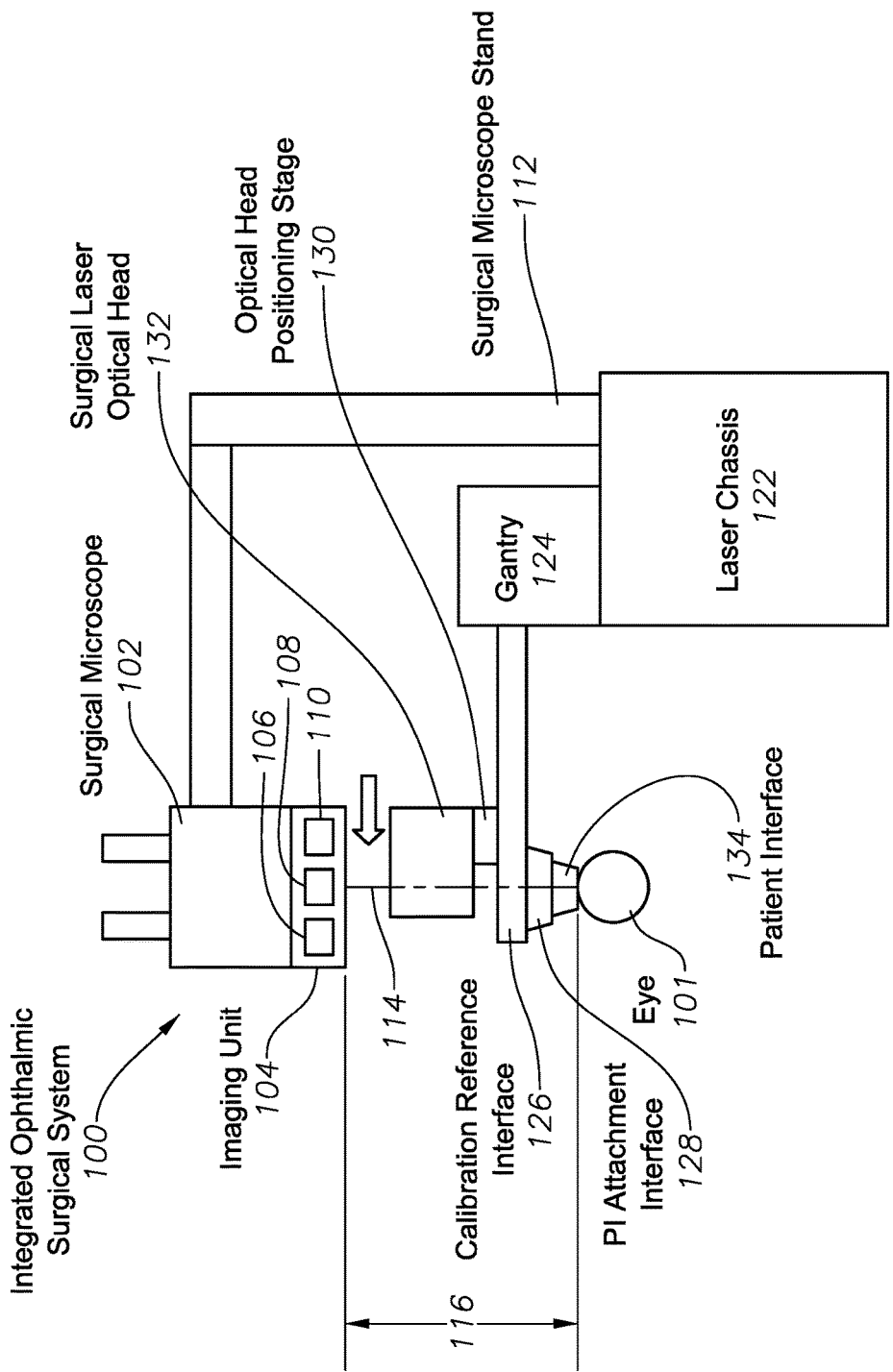

FIGS. 1D and 2D illustrate system 100 arranged in a surgical position, in which PI attachment interface 128 remains docked to eye 101, and laser optical head 132 is positioned within beam path 114 (as indicated by arrows), below surgical microscope 102 and imaging unit 104. As noted above, movement of laser optical head 132 is facilitated by positioning stage 130, which may comprise a weight balanced, vertically floating stage designed with a flexible safety buffer. Positioning stage 130 may be configured to extend, retract, rotate, or otherwise move laser optical head 132 manually or via one or more electromechanical motors based on commands from the control unit. In certain embodiments, positioning stage 130 is designed to extend or retract laser optical head 132 to pre-determined locations relative to calibration reference interface 126, to preserve validity of calibrations described above. Such pre-determined locations may include a mechanical hard stop near a distal end of calibration reference interface or a controlled location measured by position encoders.

In the surgical position of FIGS. 1D and 2D, laser optical head 132 may deliver laser pulses from the laser engine housed in laser chassis 122 to target locations within eye 101 with requisite position accuracy, focal spot quality and speed. Laser optical head 132 may be configured to deliver laser pulses under the direction of a control unit that receives imaging data from OCT system 106, image capture system 108, and/or microscope 102, analyzes the imaging data to determine a position of the eye relative to attachment interface 128 and, based on pre-stored calibration data including centering, tilt and cyclo-rotation of the eye, calculates coordinates for a treatment locations and treatment patterns within eye 101.

Figure 1E:
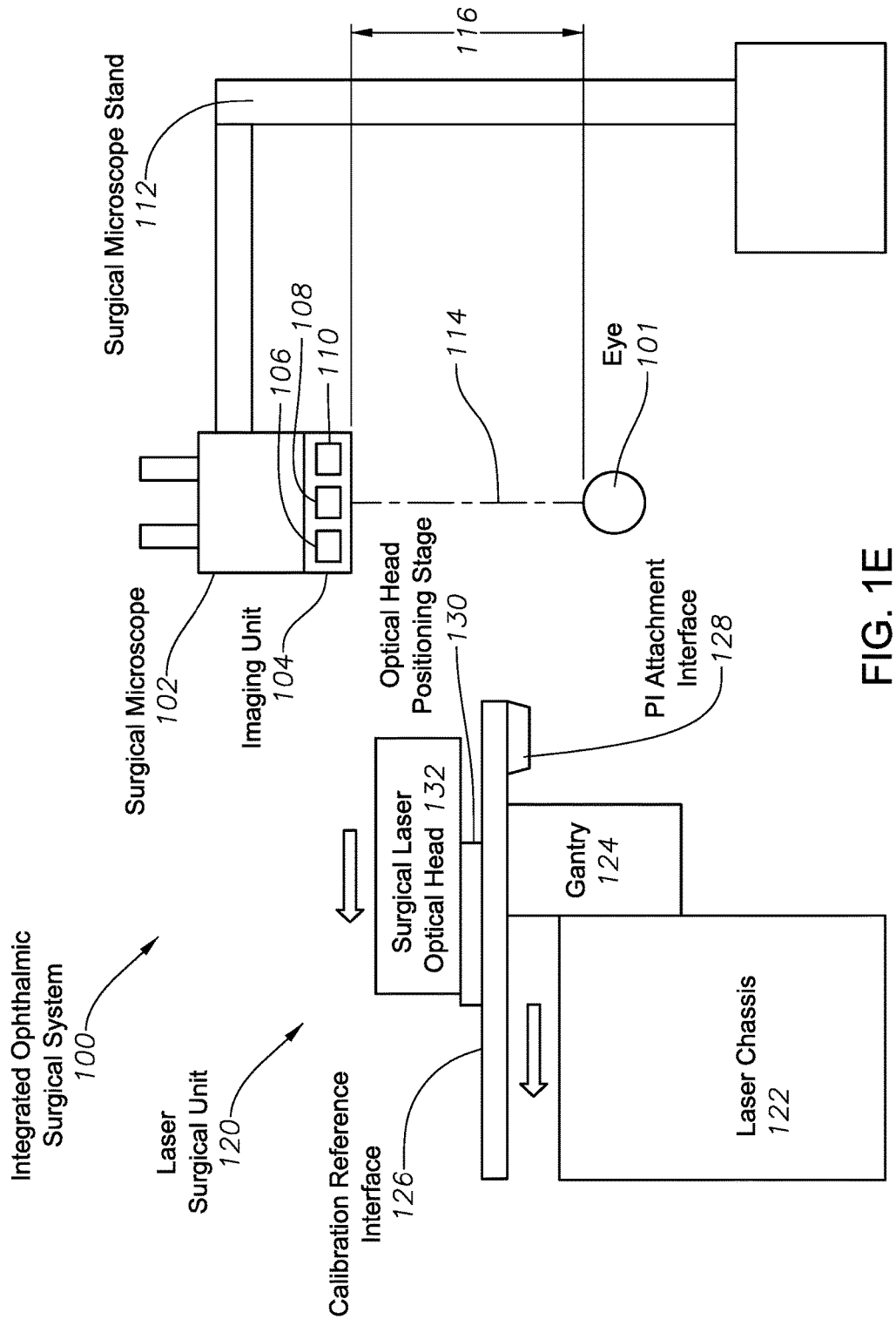
Figure 2E:
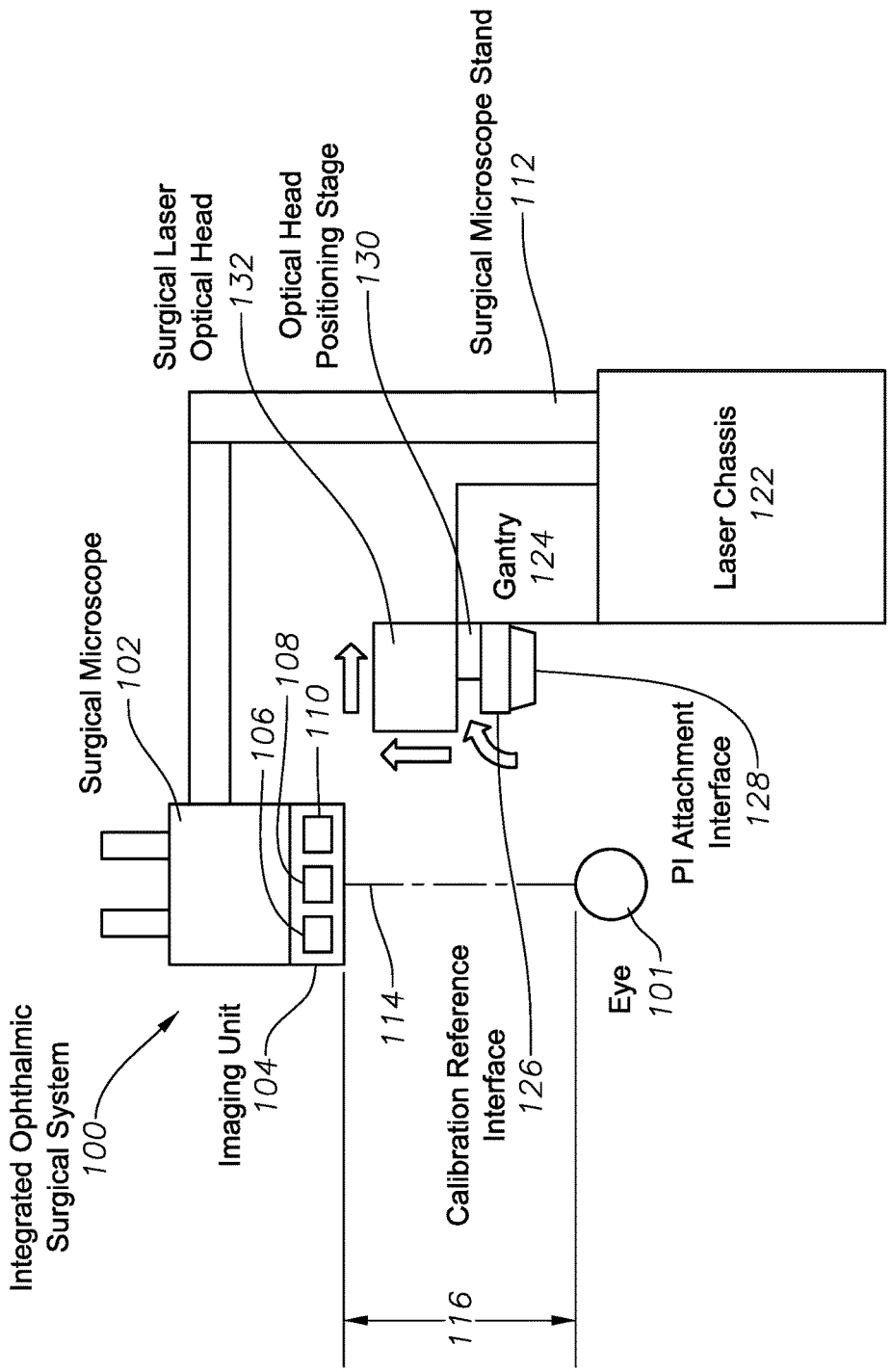

In FIG. 1E, reference interface 126, positioning stage 130, and laser optical head 132 are repositioned (here, retracted) in order to safely undock patient interface 134 provide space for the surgeon to perform a manual procedure on eye 101. FIG. 2E depicts an embodiment in which reference interface 126 is repositioned (here, rotated) to a withdrawn position, while positioning stage 130, and laser optical head 132 are retracted to provide space for the surgeon to perform a manual procedure.

FIG. 3 illustrates aspects of surgical laser optical head 132 in additional detail. In particular, laser optical head 132 may be optically coupled the laser engine via beam transportation optics 202 such as an articulating arm or optical fiber (not shown). Laser beam 200 is transmitted through transportation optics 202 toward receiving optics 204 within laser optical head 132. Receiving optics 204 receive laser beam 200, and may include one or more lenses, mirrors, cameras, or other suitable optical components. Receiving optics 204 may adjust laser beam 200 to obtain a desired beam diameter and account for any angular or positional deviation. In certain embodiments, receiving optics 204 may include a camera, processor, and memory configured to obtain and analyze the diameter and position of laser beam 200, and control steerable optics (e.g., mirrors) to actively align the beam or adjust its diameter based on real-time data. In certain embodiments, receiving optics 204 may comprise a beam conditioner.

Upon exiting receiving optics 204, laser beam 200 enters transversal scanner 206, which is configured to scan laser beam 200 laterally (e.g., in an x-y direction) with respect to optical axis 114. Laser beam 200 next enters z-scanner 208, which is configured to scan laser beam 200 to a particular z-depth along optical axis 114. Transversal scanner 206 and z-scanner 208 together provide scanning in three dimensions and may comprise any suitable configuration of lenses and/or mirrors. Examples may include any suitable arrangement of scanners, including multiple x-y or multiple z-scanners. In certain embodiments, a z-scanner is located optically upstream of an x-y-scanner. In certain embodiments, a small, fast z-scanner with relatively limited range is located optically upstream of an x-y scanner, and a larger, slower z-scanner with relatively greater range is located optically downstream of the x-y scanner. Focusing optics 210 may receive laser beam 200 from the scanners and focus the scanned beam 200 to a desired spot size. Focusing optics 210 may include one or more lenses or other suitable optical components, and may in some embodiments comprise an objective.

In addition, laser optical head 132 may include beam splitter 212 optically aligned with OCT system 106, image capture unit 108, and surgical microscope 102 when laser optical head 132 is in a surgical position, such as that shown in FIGS. 1D and 2D. Beam splitter 212 may multiplex the beam path 114 of laser beam 200, OCT system 106, image capture unit 108, and surgical microscope 102 toward eye 101. In certain embodiments, beam splitter 212 comprises a dichroic or polarization beam splitter. Beam splitter 212 and laser optical head 132 may transmit of imaging beams from surgical microscope 102, OCT system 106, and image capture unit 108 without obstruction. Thus, the focus setting of surgical microscope 102, OCT system 106, and image capture unit 108 may not be impacted when laser optical head 132 is in the surgical position shown in FIGS. 1D, 2D, 3, and 4. A surgeon may monitor the progress of the laser treatment applied by laser optical head 132 with simultaneous live OCT and video or visual observation provided by OCT system 106, image capture unit 108, display system 110, and surgical microscope 102. This may allow the surgeon (and/or the control unit of system 100) to continuously observe the target tissue in eye 101 and select appropriate treatment locations and treatment patterns based on such observations, in real time, during laser treatment. In certain embodiments, the control unit may assist with or select treatment locations and patterns based on real time image data received from OCT system 106 and image capture unit 108, and may further execute an eye tracking algorithm (e.g., feature tracking based on visible ocular features of eye 101) to assist in target selection.

FIG. 4 illustrates aspects of certain embodiments of system 100 arranged in a surgical position (e.g., FIGS. 1D and 2D) in additional detail. In particular, FIG. 4 depicts a microscope assembly head 300 that includes microscope optics 302 for a surgical microscope 102. Housed with microscope assembly head 300 are OCT system 106, which includes an OCT scanner and related optics, and image capture unit 108, which includes image capture optics and an eye tracker 304 executed by a control unit. Also included in microscope assembly head 300 are beam splitters 306, which multiplex imaging beams generated by microscope optics 302, OCT system 106, and image capture unit 108 and directs the multiplexed beam 250 toward eye 101. Microscope assembly head 300 and its components may be conceptualized as a single imaging subsystem, as indicated on the right side of the figure.

The laser subsystem below the imaging subsystem includes surgical laser optical head 132, which receives laser beam 200 from a pulsed laser engine, scans and focuses the beam via optics and scanners, as well as beam splitter 306, which multiplex the scanned laser beam 200 with imaging beams generated by microscope optics 302, OCT system 106, and image capture unit 108. The multiplexed beam is transmitted through an opening or aperture in calibration reference interface 126, though patient interface 134, and onto eye 101.

The imaging subsystem and laser subsystem may include one or more control units configured to control and functionally integrate microscope optics 302, OCT system 106, image capture unit 108, laser optical head 132, a laser engine (not shown), optical head positioning stage 103, and/or calibration reference interface 126, as described above.

As FIG. 4 illustrates, the imaging subsystem and the laser subsystem are loosely-coupled from a mechanical perspective. Accordingly, there may be relative movement between subsystems. For example, microscope assembly head 300 may be mounted to an arm of a surgical microscope stand 112 which may vibrates at various frequencies with an amplitude exceeding the required precision for a laser surgical procedure. Thus, a calibration procedure may be executed by a control unit to determine calibration variables, which may be communicated to the surgical laser optical head 132 to account for the specific position and movement of eye 101.

As further shown in FIG. 4, components of system 100, including laser optical head 132, positioning stage 130, calibration reference interface 126, and PI attachment interface 128, may fit within working distance 116 of microscope 102 and imaging unit 104 so that a laser procedure may be performed without moving or adjusting instrumentation used in a preceding diagnostic or subsequent manual procedure. In certain embodiments, reference interface 126 and optical head unit 132, in the surgical position of FIGS. 1D and 2D, together measure about or less than 300 mm vertically (along optical axis 114). This advantageously allows a surgeon to position and focus surgical microscope 102 and imaging unit 104 at a pre-operative stage for diagnostic purposes (e.g., FIGS. 1A and 1B), calibrate and align the laser optical head 132 to perform a laser procedure (e.g., FIGS. 1B-1D, 2B-2D), and then return components of laser surgical unit 120 to a withdrawn position (e.g., FIGS. 1E and 2E) to perform a manual portion of the procedure—without repositioning, refocusing, or adjusting surgical microscope 102, OCT system 106, image capture system 108, or the patient. This may permit a patient to be positioned under surgical microscope 102 at the outset of a procedure and remain there throughout the laser and manual portions of the procedure, reducing the amount of time required for the procedure.

Additionally, components of system 100 are designed to move between a pre-surgical position (e.g., FIGS. 1A, 2A), a laser surgical position (e.g., FIGS. 1D, 2D) and a manual surgical position (e.g., FIGS. 1E, 2E) within a single surgical theater. The disclosed system configuration provides a novel, compact arrangement, integrating subsystems that are conventionally separate (often located in different surgical rooms) and combining components (e.g., OCT systems) to reduce the cost and size of the surgical system. In certain embodiments, system 100 may be arranged in a single operating room and eliminate the need to move or reposition a microscope or patient between laser and manual portions of a surgical procedure. This may further reduce the length and cost of an ophthalmic surgical procedure.

Figure 5:
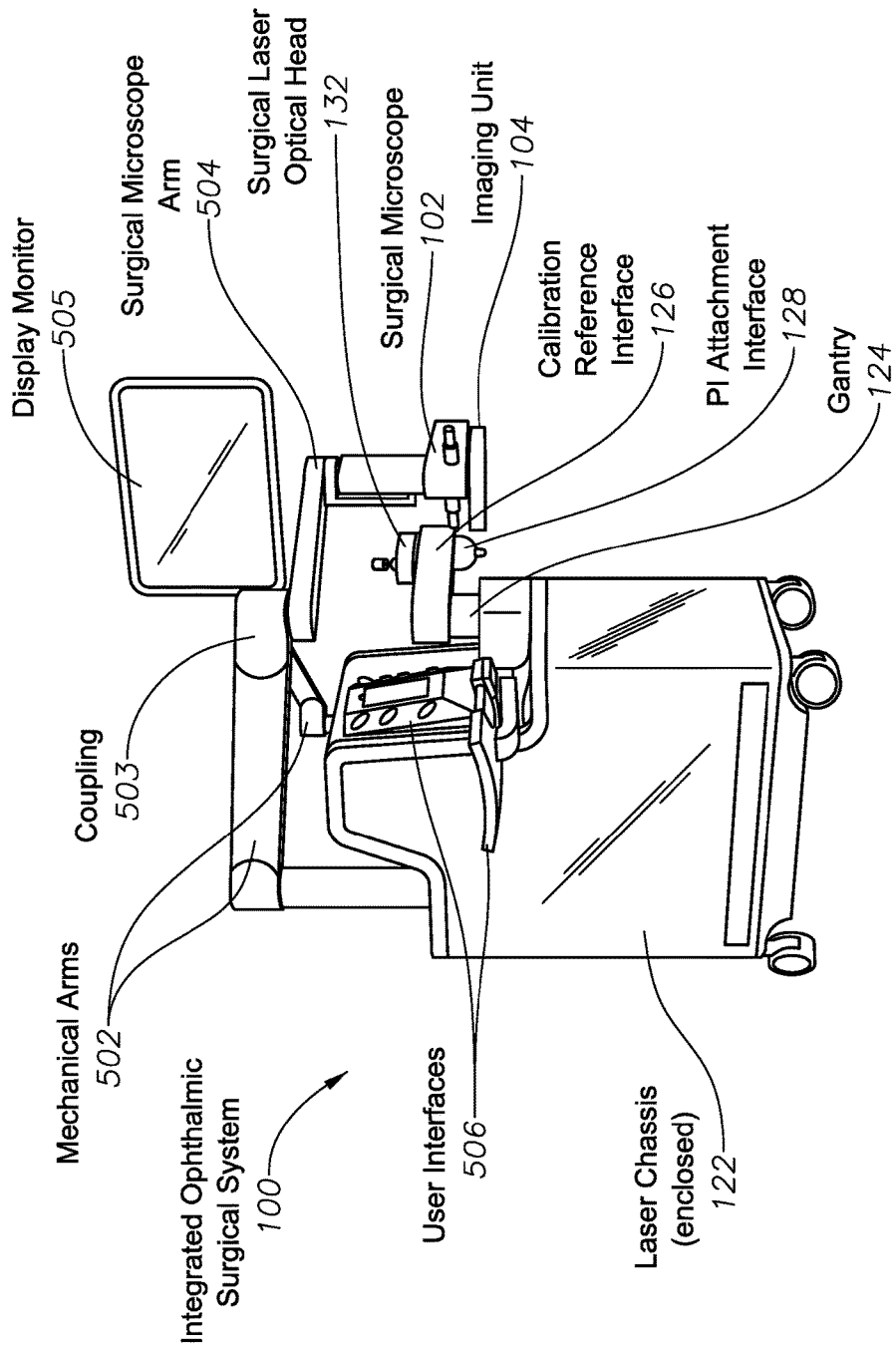
FIG. 5 illustrates aspects of an integrated ophthalmic surgical system, according to certain embodiments.

FIG. 5 illustrates an external view of particular embodiments of system 100. System 100 of FIG. 5 includes a laser chassis 122 (which sits on wheels) with an attached gantry 124. Laser chassis 122 shares an enclosure with other aspects of the system, which houses user interfaces, control units, and related components. Laser chassis 122 is coupled to gantry 124, which supports and facilitates movement of calibration reference interface 126. Attached below calibration reference interface 126 is PI attachment interface 128. An optical head positioning stage 130 (not visible in FIG. 5) is coupled to the upper side of calibration reference interface 126, and facilitates movement of laser optical head 132 to extend or retract along calibration reference interface 126. Also coupled to laser chassis 122 are two adjustable mechanical arms 502 to support a display monitor 505 and surgical microscope arm 504. Surgical microscope arm 504 supports surgical microscope 102 and imaging unit 104, which is attached to microscope 102. Mechanical arms 502 and surgical microscope arm 504 may comprise one or more translation and/or rotation stages, and may facilitate independent movement of display monitor and surgical microscope 102/imaging unit 104 in three dimensions.

During an ophthalmic surgical procedure, a patient may be positioned on his back beside laser chassis 122. A surgeon may then position and align surgical microscope 102 and imaging unit 104 with the patient's eye. Microscope 102 and an OCT system and image capture system within imaging unit 104 may then be focused and calibrated for a pre-surgical diagnostic procedure, as discussed above with respect to FIGS. 1A and 2A.

Gantry 124 includes a rotating stage, so that calibration reference interface 126 may be rotated toward the body of laser chassis 122 when not in use, and rotated out toward a patient for a laser procedure. Thus, once imaging instruments are configured and diagnostic procedures are complete, PI attachment interface 128 may be rotated such that a distal end (which may comprise an opening or aperture with distinguishing features, as noted above) is situated between surgical microscope 102/imaging unit 104 and the patient's eye, as discussed above with respect to FIGS. 1B and 2B.

A patient interface may be attached to PI attachment interface 128 and/or the patient's eye, and calibration reference interface 126 may then be lowered to dock the system to the patient's eye, as discussed above with respect to FIGS. 1C and 2C. Gantry 124 is vertically adjustable and weight balanced so that PI attachment interface 128 may be safely lowered toward and docked to a patient's eye. Movement of components during the docking process may be performed manually or via an automated process executed by a control unit. Because surgical microscope 102 and imaging unit 104 are not rigidly coupled to the surgical laser optical head 132 in the embodiment of FIG. 5, it may be necessary to calibrate such components prior to a surgical procedure. Thus, once docking is complete, the surgeon may initiate calibration procedures to calibrate surgical microscope 102 and imaging unit 104 (and components thereof) to surgical laser optical head 132, as discussed above. During calibration, surgical laser optical head 132 may be retracted toward the end of calibration reference interface 126 proximal to laser chassis 122, or extended toward a distal end of calibration reference interface 126.

Once subsystems are calibrated, surgical laser optical head 132 may be extended toward a distal end of calibration reference interface 126 via optical head positioning stage 130 (if necessary) to a surgical position. In the surgical position, surgical microscope 102 and the OCT system and image capture system within imaging unit 104 are optically aligned, and the optical beam path of those systems is multiplexed via a beam splitter in laser optical head 132 with a pulsed laser beam generated by a laser engine in laser chassis 122, as explained above with respect to FIGS. 1D, 2D, 3, and 4. Once the laser procedure is complete, laser optical head 132 may be retracted, and calibration reference interface 126 may be rotated to a compact withdrawn position to provide the surgeon ample space to begin and conduct a manual surgical procedure, without moving the patient or re-adjusting microscope 102, or the OCT system and image capture system in imaging unit 104.

Accordingly, embodiments of the disclosure combine a surgical microscope and imaging systems used in a manual procedure with a laser surgical unit used in a laser procedure according to a novel configuration that enables a surgeon to transition from a diagnostic stage to a laser procedure and then to a manual procedure without moving the patient and without the need to repositioning, refocusing, or adjust a surgical microscope, OCT system, or image capture system 108 after the laser procedure.

It will be appreciated that various of the above-disclosed and other features and functions, or alternatives thereof, may be desirably combined into many other different systems or applications. It will also be appreciated that various presently unforeseen or unanticipated alternatives, modifications, variations or improvements therein may be subsequently made by those skilled in the art which alternatives, variations and improvements are also intended to be encompassed by the following claims.

What is claimed is:
1. An ophthalmic laser surgical system, comprising:
a chassis comprising a pulsed laser source configured to generate a laser beam of laser pulses;
a gantry coupled to the chassis, wherein the position of the gantry with respect to the chassis is adjustable;
a reference interface coupled to the gantry, wherein:
the reference interface comprises an attachment interface configured to couple to a patient interface for docking with an eye, the attachment interface located at a distal portion of the reference interface; and
the reference interface is configured to move to a first reference interface position in which the attachment interface is proximal to the chassis and a second reference interface position in which the attachment interface is distal from the chassis;
an optical head unit coupled to the reference interface, wherein:
the optical head unit comprises:
a laser scanner configured to scan the scan the laser beam of pulsed laser pulses to a target region of an eye docked to the patient interface; and
a beam splitter configured to multiplex the scanned laser beam of pulsed laser pulses with an imaging beam path of an external imaging system; and
the optical head unit is configured to move to a first optical head unit position near a proximal end of the reference interface and a second optical head unit position which is a lockable surgical position near a distal end of the reference interface.

2. The laser surgical system of claim 1, wherein the reference interface is configured to move to the first reference interface position and the second reference position by at least one of: extending, retracting, rotating, or swiveling.

3. The laser surgical system of claim 1, wherein the optical head unit is configured to move to the first optical head unit position and the second optical head unit position by at least one of: extending, retracting, rotating, or swiveling.

4. The laser surgical system of claim 1, wherein the external imaging system is an optical coherence tomography (OCT) imaging system or a surgical microscope, and wherein the laser surgical system and the external imaging system are not rigidly coupled, such that the laser surgical system and the external imaging system vibrate independently.

5. The laser surgical system of claim 1, wherein the external imaging system is an optical coherence tomography (OCT) imaging system or a surgical microscope, and wherein the laser surgical system and the external imaging system are not rigidly coupled, such that a movement of the laser surgical system with respect to the external imaging system greater than an accuracy requirement for the laser surgical system.

6. The laser surgical system of claim 1, wherein the reference interface and optical head unit together measure no more than 300 mm vertically along an optical axis of the external imaging system when the optical head unit is in the second optical head unit position.

7. The laser surgical system of claim 1, wherein:
the attachment interface is optically aligned with the imaging beam path of the external imaging system when the reference interface is in the second reference interface position; and
the beam splitter is optically aligned with the imaging beam path of the external imaging system when the optical head unit is in the second optical head unit position.

8. The laser surgical system of claim 1, wherein the reference interface structure comprises an arm, a shelf, or a plate.

9. The laser surgical system of claim 1, further comprising a control unit communicatively coupled to the optical head unit and the external imaging system, the control unit comprising a processor configured to:
receive imaging data from the surgical microscope and the external imaging system;
based on the received imaging data, determine a position of the eye relative to the attachment interface; and
based on the determined position, control the optical head unit to scan the laser beam of pulsed laser pulses to the target region of the eye.

10. An ophthalmic surgical system, comprising:
a surgical microscope configured to generate an image of an eye;
an optical coherence tomography (OCT) imaging system configured to generate an OCT image of the eye, wherein the OCT imaging system is integrated and optically aligned with the surgical microscope;
an image capture unit configured to receive and process the images generated by the surgical microscope and the OCT imaging system;
a laser surgical system comprising:
a chassis comprising a pulsed laser source configured to generate a laser beam of laser pulses;
a gantry coupled to the chassis, wherein the position of the gantry with respect to the chassis is adjustable;
a reference interface structure coupled to the gantry, wherein:
the reference interface comprises an attachment interface configured to couple to a patient interface for docking with an eye, the attachment interface located at a distal portion of the reference interface; and
the reference interface is configured to move to a first reference interface position in which the attachment interface is proximal to the chassis and a second reference interface position in which the attachment interface is distal from the chassis and is optically aligned with the imaging beam path of the surgical microscope and OCT imaging system;
an optical head unit coupled to the reference interface, wherein:
the optical head unit comprises:
a laser scanner configured to scan the laser beam of pulsed laser pulses to a target region of an eye docked to the patient interface; and
a beam splitter configured to multiplex the scanned laser beam of pulsed laser pulses with an imaging beam path of the surgical microscope and the OCT imaging system; and
the optical head unit is configured to move to a first optical head unit position near a proximal end of the reference interface and a second optical head unit position which is a lockable surgical position near a distal end of the reference interface; and
a control unit communicatively coupled to the optical head unit and the image capture unit, the control unit comprising a processor configured to:
receive imaging data from the surgical microscope and image capture unit; and
based on the received imaging data, determine a position of the eye relative to the attachment interface; and
based on the determined position, control the optical head unit to scan the laser beam of pulsed laser pulses to the target region of the eye.

11. The laser surgical system of claim 10, wherein the reference interface is configured to move to the first reference interface position and the second reference position by at least one of: extending, retracting, rotating, or swiveling.

12. The laser surgical system of claim 10, wherein the optical head unit is configured to move to the first optical head unit position and the second optical head unit position by at least one of: extending, retracting, rotating, or swiveling.

13. The ophthalmic surgical system of claim 10, wherein the beam splitter is optically aligned with the imaging beam path of the surgical microscope and OCT imaging system when the optical head unit is in the second optical head unit position.

14. The ophthalmic surgical system of claim 10, wherein the beam splitter is configured to multiplex the laser beam with the imaging beam path of the surgical microscope and the OCT imaging system without changing a focus or position of the surgical microscope or the OCT imaging system.

15. The ophthalmic surgical system of claim 10, wherein the laser surgical system and the OCT imaging system are not rigidly coupled, such that the laser surgical system and the OCT imaging system vibrate independently.

16. The ophthalmic surgical system of claim 10, wherein the laser surgical system and the OCT imaging system are not rigidly coupled, such that movement of the laser surgical system with respect to the OCT imaging system is greater than an accuracy requirement for the laser surgical system.

17. The laser surgical system of claim 1, wherein the reference interface and optical head unit together measure no more than 300 mm vertically along an optical axis of the OCT imaging system when the optical head unit is in the second optical head unit position.

18. The laser surgical system of claim 10, wherein the optical head unit is configured to move to the second optical head unit position and cause the laser scanner to scan the laser beam of pulsed laser pulses to the target region of the eye docked to the patient interface without moving or changing a working distance of the surgical microscope or OCT imaging system.

19. The laser surgical system of claim 10, wherein the reference interface structure comprises an arm, a shelf, or a plate.

20. The laser surgical system of claim 10, wherein the processor of the control unit is further configured to calculate a centering, tilt and cyclo-rotation of the eye, based on the determined position of the eye relative to the attachment interface.

* * * * *